United States Patent
Houze et al.

(10) Patent No.: US 7,465,804 B2
(45) Date of Patent: *Dec. 16, 2008

(54) COMPOUNDS, PHARMACEUTICAL COMPOSITIONS AND METHODS FOR THEIR USE IN TREATING METABOLIC DISORDERS

(75) Inventors: Jonathan Houze, San Mateo, CA (US); Jiwen Liu, Foster City, CA (US); Zhihua Ma, San Mateo, CA (US); Julio C. Medina, San Carlos, CA (US); Michael J. Schmitt, San Francisco, CA (US); Rajiv Sharma, Fremont, CA (US); Ying Sun, Albany, CA (US); Yingcai Wang, Fremont, CA (US); Liusheng Zhu, Burlingame, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/436,732

(22) Filed: May 17, 2006

(65) Prior Publication Data

US 2006/0270724 A1    Nov. 30, 2006

Related U.S. Application Data

(60) Provisional application No. 60/683,331, filed on May 20, 2005.

(51) Int. Cl.
*C07D 263/32* (2006.01)
*C07D 257/04* (2006.01)
*C07D 249/04* (2006.01)
*C07D 249/08* (2006.01)
*C07D 277/22* (2006.01)
*C07D 277/24* (2006.01)
*C07C 59/13* (2006.01)

(52) U.S. Cl. .................. 548/235; 548/253; 548/268.6; 548/204; 562/472; 562/469

(58) Field of Classification Search ............... 548/235, 548/341.1, 341.5, 253, 268.6, 204, 205; 562/472, 469
See application file for complete search history.

(56) References Cited

U.S. PATENT DOCUMENTS

| | | | |
|---|---|---|---|
| 4,760,089 A | 7/1988 | Chambers et al. | |
| 6,037,367 A | 3/2000 | Christensen, IV et al. | |
| 6,476,052 B1 * | 11/2002 | Muller et al. | 514/323 |
| 6,506,757 B1 | 1/2003 | Tajima et al. | |
| 6,710,063 B1 | 3/2004 | Chao et al. | |
| 6,723,740 B2 | 4/2004 | Chao et al. | |
| 6,875,780 B2 | 4/2005 | Auerbach et al. | |
| 6,939,875 B2 | 9/2005 | Auerbach et al. | |
| 6,964,983 B2 | 11/2005 | Auerbach et al. | |
| 7,338,960 B2 | 3/2008 | Bell et al. | |
| 7,345,068 B2 | 3/2008 | Endou et al. | |
| 2004/0058965 A1 | 3/2004 | Momose et al. | |
| 2005/0119256 A1 | 6/2005 | Endo et al. | |
| 2006/0003344 A1 | 1/2006 | Houseknecht et al. | |
| 2006/0004012 A1 * | 1/2006 | Akerman et al. | 514/249 |
| 2007/0142384 A1 | 6/2007 | Akerman et al. | |
| 2007/0265332 A1 | 11/2007 | Ge et al. | |

FOREIGN PATENT DOCUMENTS

| | | |
|---|---|---|
| CA | 2111035 | 6/1994 |
| DE | 27 33 305 | 7/1977 |
| DE | 42 41 632 A1 | 6/1994 |
| DE | 199 4 1 567 A1 | 4/2000 |
| EP | 0 250 264 | 12/1987 |
| EP | 1 357 115 A1 | 10/2003 |
| EP | 1 380 562 | 1/2004 |
| EP | 1 535 915 A1 | 6/2005 |
| EP | 1 559 422 A1 | 8/2005 |
| EP | 1 630 152 A1 | 3/2006 |
| JP | 10316641 | 2/1998 |
| WO | WO 93/23040 | 11/1993 |
| WO | WO 93/23041 | 11/1993 |
| WO | WO 95/01326 | 1/1995 |
| WO | WO 95/01348 | 1/1995 |
| WO | WO 97/12867 | 4/1997 |
| WO | WO 00/68223 | 11/2000 |
| WO | WO 01/00603 | 1/2001 |
| WO | WO 01/36351 | 5/2001 |

(Continued)

OTHER PUBLICATIONS

U.S. Appl. No. 11/067,377, filed Feb. 2005, Akerman, et al.*

(Continued)

*Primary Examiner*—Kamal A Saeed
*Assistant Examiner*—Shawquia Young
(74) *Attorney, Agent, or Firm*—Bernard P. Friedrichsen

(57) ABSTRACT

The present invention provides compounds useful, for example, for modulating insulin levels in a subject, having the general formula I:

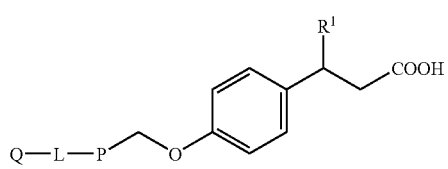

wherein Q is an optionally substituted phenyl; L is a bond or O; P is a benzene or an optionally substituted thiazole ring; and $R^1$ has the values provided herein. The present invention also provides compositions, uses, and methods for use of the compounds, for instance, for treatment of type II diabetes.

48 Claims, No Drawings

FOREIGN PATENT DOCUMENTS

| | | |
|---|---|---|
| WO | WO 01/36365 | 5/2001 |
| WO | WO 02/053547 | 7/2002 |
| WO | WO 02/057783 | 7/2002 |
| WO | WO 02/062774 | 8/2002 |
| WO | WO 02/100403 | 12/2002 |
| WO | WO 02/100812 | 12/2002 |
| WO | WO 03/068959 | 8/2003 |
| WO | WO 03/074050 | 9/2003 |
| WO | WO 03/099793 | 12/2003 |
| WO | WO 2004/000315 | 12/2003 |
| WO | WO 2004/022551 | 3/2004 |
| WO | WO 2004/041266 | 5/2004 |
| WO | WO 2004/106276 | 12/2004 |
| WO | WO 2005/051890 | 6/2005 |
| WO | WO 2005/058848 | 6/2005 |
| WO | WO 2005/063725 | 7/2005 |
| WO | WO 2005/063729 | 7/2005 |
| WO | WO 2005/086661 | 9/2005 |
| WO | WO 2005/087710 | 9/2005 |
| WO | WO 2006/001092 | 1/2006 |
| WO | WO 2006/011615 | 2/2006 |
| WO | WO 2007/123225 | 11/2007 |
| WO | WO 2007/131619 | 11/2007 |
| WO | WO 2007/131620 | 11/2007 |
| WO | WO 2007/131622 | 11/2007 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online], [retrieved on Jul. 6, 2007]. Retrieved from the Internet, URL; http://en.wikipedia.org/wiki/Cancer>.*
Vippagunta, et al. Advanced Drug Delivery Reviews, 48 (2001), 3-26.*
Kotarsky et al., "A Human Cell Surface Receptor Activated by Free Fatty Acids and Thiazolidinedione Drugs", *Biochemical and Biophysical Research Communications*, 301, 406-410 (2003).
Sawzdargo et al., "A Cluster of Four Novel Human G Protein-Coupled Receptor Genes Occurring in Close Proximity to CD22 Gene on Chromosome 19q13.1", *Biochemical and Biophysical Research Communications*, 239, 543-547 (1997).
Berthelot et al., "Synthesis and Pharmalogical Evaluation of γ-Aminobutyric Acid Analogues. New Ligand for $GABA_B$ Sites," *J. Med. Chem.*, 30, 743-746 (1987).
Briscoe et al., "The Orphan G Protein-Coupled Receptor GPR40 is Activated by Medium and Long Chain Fatty Acids," *J. of Biol. Chem.*, 278(13), 11303-11311 (2003).
DeWolf et al., "Inactivation of Dopamine β-Hydroxylase by β-Ethynyltyramine: Kinetic Characterization and Covalent Modification of an Active Site Peptide," *Biochemistry*, 28, 2833-2842 (1989).
Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency,"*J. Med. Chem.*, 33, 2828-2841 (1990).

Haigh et al., "Non-thiazolidinedione Antihyperglycaemic Agents. Part 3: The Effects of Stereochemistry on the Potency of α-Methoxy-β-phenylpropanoic Acids," *Bioorg. & Med. Chem.*, 7, 821-830 (1999).
Ishikawa et al., "Actions of the Novel Oral Antidiabetic Agent HQL-975 in Insulin-Resistant Non-Insulin—Dependent diabetes Mellitus Model Animals," *Diabetes Res. and Clin. Pract.*, 41, 101-111 (1998).
Ishikawa et al., "Effects of the Novel Oral Antidiabetic Agent HQL-975 on Glucose and Lipid Metabolism in Diabetic db/db Mice," *Arzneim. Forsch. Drug Res.*, 48(3), 245-250 (1998).
Itoh et al., "Free Fatty Acids Regulate Insulin Secretion from Pancreatic β Cells Through GPR40," *Nature*, 422, 173-176 (2003).
Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).
Iizuka et al., "β-Substituted Phenethylamines as High Affinity Mechanism-Based Inhibitors of Dopamine β-Hydroxylase," *J. Med. Chem.*, 31, 704-706 (1988).
Kuchar et al., "Benzyloxyarylaliphatic Acids: Synthesis and Quantitative Relations Between Structure and Antiinflammatory Activity," *Collection Czechoslovak Chem, Commun.*, 47, 2514-2524 (1982).
Kuchar et al., "The Effects of Lopophilicity on the Inhibition of Denaturation of Serum Albumin and on the Activation of Fibrionolysis Observed with a Serixes of Benzyloxyarylaliphatic Acids," *Collection Czechoslovak Chem, Commun.*, 48, 1077-1088 (1983).
Liu et al., "Synthesis and biological Activity of L-Tyrosine-based PPARγ Agonists with Reduced Molecular Weight," *Bioorg. & Med. Chem. Lett.*, 11, 3111-3113 (2001).
Oliver et al., A Selective Peroxisome Proliferator-Activated Receptor δ Agonist Promotes Reverse Cholesterol Transport,: *PNAS*, 98(9), 5306-5311 (2001).
Poitout, Vincent, "The Ins and Outs of Fatty Acids on the Pancreatic β Cells," *Trends in Encocrinology and Metabolism*, 14(5), 201-203 (2003).
Shaw et al., "Enantioselective Synthesis of (+)-(2S, 3S)-3-Ethyltyrosine," *Tetrahedron Letters*, 31(35), 5081-84 (1990).
Waid et al., "Constrained Amino Acids. An Approach to the Synthesis of 3-Substituted Prolines," *Tetrahedron Letters*, 37(24), 4091-4094 (1996).
Dulce M. Garrido et al., "Synthesis and activity of small molecule GPR40 agonists," Bioorganic & Medicinal Chemistry Letters, 16, 1840-1845 (2006).
International Search Report and Written Opinion from copending PCT/US2006/019545 (2007).
Supplementary Partial European Search Report for copending EP 05723623 by European Patent Office completed on Sep. 7, 2007.
Booth, C. J. et al., "The Synthesis and Transition Temperatures of Novel Low Molar Mass Chosesteric materials Derives from (R)-2-(4-Hydroxyphenoxy)propanoic Acid," Mol. Cryst. Liq. Cryst., vol. 210, pp. 31-57(1992).
Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).

* cited by examiner

COMPOUNDS, PHARMACEUTICAL COMPOSITIONS AND METHODS FOR THEIR USE IN TREATING METABOLIC DISORDERS

1. CROSS REFERENCES TO RELATED APPLICATIONS

This application claims the benefit of U.S. Provisional Application No. 60/683,331, filed on May 20, 2005, which is incorporated herein by reference in its entirety and for all purposes as if fully set forth herein.

2. FIELD OF THE INVENTION

The present invention relates to compounds capable of modulating the G-protein-coupled receptor GPR40, compositions comprising the compounds, and methods and uses for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al., Biochem. Biophys. Res. Commun. 239:543-547 (1997). GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al., Nature 422 :173-176 (2003); Briscoe et al., J. Biol. Chem. 278:11303-11311 (2003); Kotarsky et al., Biochem. Biophys. Res. Commun. 301: 406-410 (2003).

The prevalence of type II diabetes, obesity, hypertension, cardiovascular disease and dyslipidemia underscores the need for new therapies to effectively treat or prevent these conditions.

4. SUMMARY OF THE INVENTION

Provided herein are compounds, pharmaceutical compositions and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema. The use of the compounds in treating or preventing such conditions or disorders and the use of such compounds in the preparation of medicaments for treating or preventing such conditions or disorders is also provided.

In one aspect, the invention provides compounds having formula I:

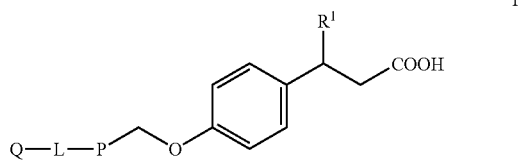

wherein Q is an optionally substituted phenyl; L is a bond or O (an oxygen atom); P is benzene or an optionally substituted thiazole; $R^1$ is an optionally substituted oxazolyl, imidazolyl, triazolyl, or tetrazolyl or —C(O)NR²R³; and $R^2$ and $R^3$ are independently selected from hydrogen and $(C_1-C_4)$alkyl.

In certain embodiments, $R^1$ is selected from an optionally substituted imidazolyl or an optionally substituted triazolyl. In some such embodiments, $R^1$ is selected from 1-methyl-1H-imidazol-2-yl or 2-methyl-2H-1,2,4-triazol-3-yl.

In certain embodiments, $R^1$ is selected from an optionally substituted oxazolyl other than 5-methyl-oxazol-2-yl, an optionally substituted tetrazolyl, or —C(O)NR²R³. In some such embodiments, $R^1$ is not dimethylcarbamyl or —C(═O)NH₂ when Q is 4-trifluoromethyl-phenyl, P is benzene and L is a bond. In some embodiments, $R^1$ is not an unsubstituted tetrazolyl when Q is 4-trifluoromethyl-phenyl, P is benzene and L is a bond. In some embodiments, $R^1$ is selected from dimethylcarbamyl, oxazol-2-yl, or 1-methyl-1H-tetrazol-5-yl.

In certain embodiments, L is a bond. In other embodiments, L is O.

In certain embodiments, Q is an unsubstituted phenyl. In certain other embodiments, Q is a phenyl substituted with one or two substituents independently selected from methyl, trifluoromethyl, halogen, methoxy, ethoxy, butoxy and hydroxyl. In some embodiments, Q is selected from 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, 4-methyl-phenyl or unsubstituted phenyl. In some embodiments, Q is an unsubstituted phenyl and L is O. In other embodiments, Q is a substituted phenyl and L is a bond.

In certain embodiments, the compound of formula I provided is a mixture of S— and R-enantiomers. In other embodiments, the compound is provided as the S enantiomer whereas in other embodiments, the compound is provided as the R enantiomer.

In some embodiments, the compound of formula I provided is a stereomerically pure enantiomer having formula Ia or Ib:

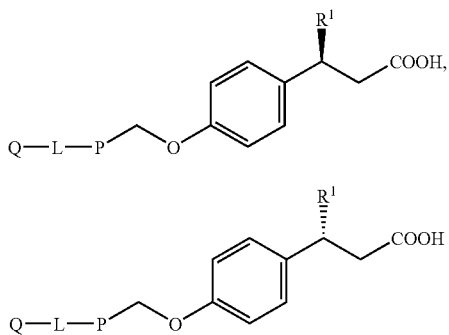

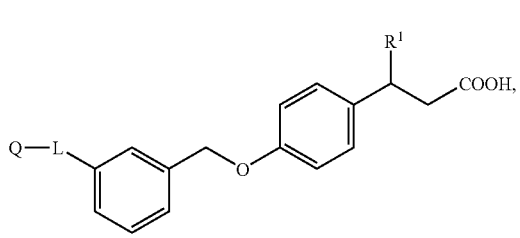

wherein Q, L, P and R$^1$ are as defined above.

In certain embodiments, the compound of the invention has formula II or III:

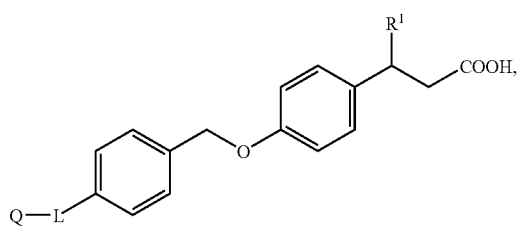

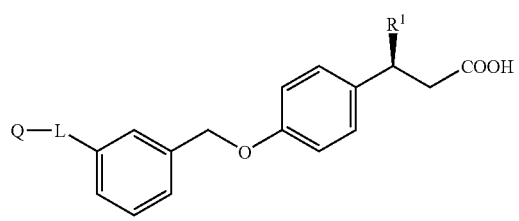

wherein Q, L and R$^1$ are as defined in formula I above. In some such embodiments, the compound has the formula IIA or IIIa:

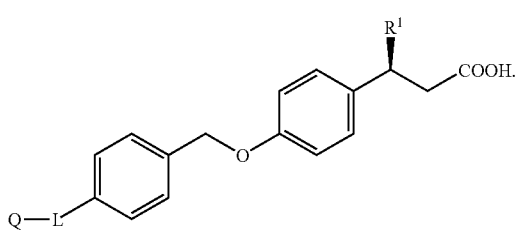

In certain embodiments, the compound of the invention has formula IV:

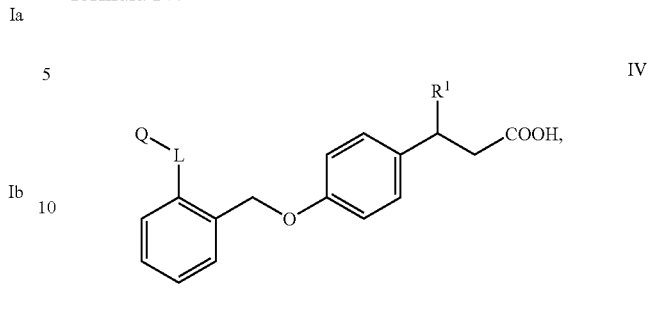

wherein Q, L and R$^1$ are as defined in formula I above.

In certain embodiments, the compound of the invention has formula V:

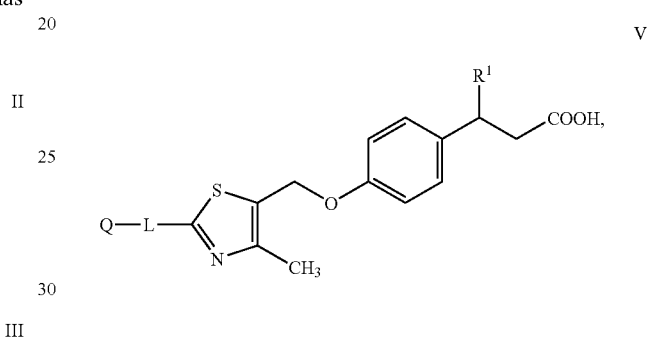

wherein Q, L and R$^1$ are as defined in formula I above. In some such embodiments, the compound has the formula Va:

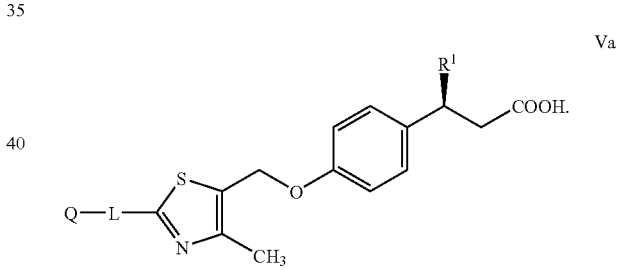

In certain embodiments, the compound is (S)-3-[4-(4'-chloro-2'-methyl-biphenyl-3-ylmethoxy)-phenyl]-N,N-dimethyl-succinamic acid; (S)-3-[4-(4'-chloro-2'-methyl-biphenyl-3-ylmethoxy)-phenyl]-3-(1-methyl-1H-imidazol-2-yl)-propionic acid; (S)-3-[4-(4'-chloro-2'-methyl-biphenyl-3-ylmethoxy)-phenyl]-3-(2-methyl-2H-1,2,4-triazol-3-yl)-propionic acid; (S)-3-[4-(4'-chloro-2'-methyl-biphenyl-3-ylmethoxy)-phenyl]-3-(1-methyl-1H-tetrazol-5-yl)-propionic acid; (S)-3-[4-(2'-butoxy-5'-methyl-biphenyl-4-ylmethoxy)-phenyl]-3-(2-methyl-2H-1,2,4-triazol-3-yl)-propionic acid; (S)-N,N-dimethyl-3-[4-(4-methyl-2-p-tolyl-thiazol-5-ylmethoxy)-phenyl]-succinamic acid; or (S)-3-(1-methyl-1H-tetrazol-5-yl)-3-[4-(4-methyl-2-p-tolyl-thiazol-5-ylmethoxy)-phenyl]-propionic acid.

In certain embodiments, the compound is (S)-N,N-Dimethyl-3-[4-(3-phenoxy-benzyloxy)-phenyl]-succinamic acid; (S)-3-Oxazol-2-yl-3-[4-(3-phenoxy-benzyloxy)-phenyl]-propionic acid; (S)-3-(1-Methyl-1H-imidazol-2-yl)-3-[4-(3-phenoxy-benzyloxy)-phenyl]-propionic acid; (S)-3-(2-Methyl-2H-1,2,4-triazol-3-yl)-3-[4-(3-phenoxy-benzyloxy)-phenyl]-propionic acid; (S)-3-(1-Methyl-1H- tetrazol-5-yl)-3-[4-(3-phenoxy-benzyloxy)-phenyl]-propionic acid; (S)-N,N-Dimethyl-3-[4-(4-phenoxy-benzyloxy)-phenyl]-succinamic acid; (S)-3-Oxazol-2-yl-3-[4-(4-phenoxy-benzyloxy)-phenyl]-propionic acid; (S)-3-(1-Methyl-1 H-imidazol-2-yl)-3-[4-(4-phenoxy-benzyloxy)-phenyl]-propionic acid; (S)-3-(2-Methyl-2H-1,2,4-triazol-3-yl)-3-[4-(4-phenoxy-benzyloxy)-phenyl]-propionic acid; or (S)-3-(1-Methyl-1H-tetrazol-5-yl)-3-[4-(4-phenoxy-benzyloxy)-phenyl]-propionic acid.

In certain embodiments, the compound is (S)-3-Oxazol-2-yl-3-[4-(4'-trifluoromethyl-biphenyl-3-ylmethoxy)-phenyl]-propionic acid; (S)-3-(1-Methyl-1H-imidazol-2-yl)-3-[4-(4'-trifluoromethyl-biphenyl-3-ylmethoxy)-phenyl]-propionic acid; (S)-3-(2-Methyl-2H-1,2,4-triazol-3-yl)-3-[4-(4'-trifluoromethyl-biphenyl-3-ylmethoxy)-phenyl]-propionic acid; (S)-3-(1-Methyl-1H-tetrazol-5-yl)-3-[4-(4'-trifluoromethyl-biphenyl-3-ylmethoxy)-phenyl]-propionic acid; (S)-3-[4-(3'-Chloro-2'-methyl-biphenyl-3-ylmethoxy)-phenyl]-N,N-dimethyl-succinamic acid; (S)-3-[4-(3'-Chloro-2'-methyl-biphenyl-3-ylmethoxy)-phenyl]-3-oxazol-2-yl-propionic acid; (S)-3-[4-(3'-Chloro-2'-methyl-biphenyl-3-ylmethoxy)-phenyl]-3-(1-methyl-1H-imidazol-2-yl)-propionic acid; (S)-3-[4-(3'-Chloro-2'-methyl-biphenyl-3-ylmethoxy)-phenyl]-3-(2-methyl-2H-1,2,4-triazol-3-yl)-propionic acid; (S)-3-[4-(3'-Chloro-2'-methyl-biphenyl-3-ylmethoxy)-phenyl]-3-(1-methyl-1H-tetrazol-5-yl)-propionic acid; (S)-3-[4-(4'-Chloro-2'-methyl-biphenyl-3-ylmethoxy)-phenyl]-N,N-dimethyl-succinamic acid; (S)-3-[4-(4'-Chloro-2'-methyl-biphenyl-3-ylmethoxy)-phenyl]-3-oxazol-2-yl-propionic acid; (S)-3-[4-(4'-Chloro-2'-methyl-biphenyl-3-ylmethoxy)-phenyl]-3-(1-methyl-1H-imidazol-2-yl)-propionic acid; (S)-3-[4-(4'-Chloro-2'-methyl-biphenyl-3-ylmethoxy)-phenyl]-3-(2-methyl-2H-1,2,4-triazol-3-yl)-propionic acid; (S)-3-[4-(4'-Chloro-2'-methyl-biphenyl-3-ylmethoxy)-phenyl]-3-(1-methyl-1H-tetrazol-5-yl)-propionic acid; (S)-3-[4-(5'-Chloro-2'-methyl-biphenyl-3-ylmethoxy)-phenyl]-N,N-dimethyl-succinamic acid; (S)-3-[4-(5'-Chloro-2'-methyl-biphenyl-3-ylmethoxy)-phenyl]-3-oxazol-2-yl-propionic acid; (S)-3-[4-(5'-Chloro-2'-methyl-biphenyl-3-ylmethoxy)-phenyl]-3-(1-methyl-1H-imidazol-2-yl)-propionic acid; (S)-3-[4-(5'-Chloro-2'-methyl-biphenyl-3-ylmethoxy)-phenyl]-3-(2-methyl-2H-1,2,4-triazol-3-yl)-propionic acid; (S)-3-[4-(5'-Chloro-2'-methyl-biphenyl-3-ylmethoxy)-phenyl]-3-(1-methyl-1H-tetrazol-5-yl)-propionic acid; (S)-3-[4-(2'-Butoxy-5'-methyl-biphenyl-4-ylmethoxy)-phenyl]-N,N-dimethyl-succinamic acid; (S)-3-[4-(2'-Butoxy-5'-methyl-biphenyl-4-ylmethoxy)-phenyl]-3-oxazol-2-yl-propionic acid; (S)-3-[4-(2'-Butoxy-5'-methyl-biphenyl-4-ylmethoxy)-phenyl]-3-(1-methyl-1H-imidazol-2-yl)-propionic acid; (S)-3-[4-(2'-Butoxy-5'-methyl-biphenyl-4-ylmethoxy)-phenyl]-3-(2-methyl-2H-1,2,4-triazol-3-yl)-propionic acid; (S)-3-[4-(2'-Butoxy-5'-methyl-biphenyl-4-ylmethoxy)-phenyl]-3-(1-methyl-1H-tetrazol-5-yl)-propionic acid; (S)-3-[4-(3'-Ethoxy-biphenyl-4-ylmethoxy)-phenyl]-N,N-dimethyl-succinamic acid; (S)-3-[4-(3'-Ethoxy-biphenyl-4-ylmethoxy)-phenyl]-3-oxazol-2-yl-propionic acid; (S)-3-[4-(3'-Ethoxy-biphenyl-4-ylmethoxy)-phenyl]-3-(1-methyl-1H-imidazol-2-yl)-propionic acid; (S)-3-[4-(3'-Ethoxy-biphenyl-4-ylmethoxy)-phenyl]-3-(2-methyl-2H-1,2,4-triazol-3-yl)-propionic acid; or (S)-3-[4-(3'-Ethoxy-biphenyl-4-ylmethoxy)-phenyl]-3-(1-methyl-1H-tetrazol-5-yl)-propionic acid.

In still other embodiments, the compound is (S)-N,N-Dimethyl-3-{4-[4-methyl-2-(4-trifluoromethyl-phenyl)-thiazol-5-ylmethoxy]-phenyl}-succinamic acid; (S)-3-{4-[4-Methyl-2-(4-trifluoromethyl-phenyl)-thiazol-5-ylmethoxy]-phenyl}-3-oxazol-2-yl-propionic acid; (S)-3-(1-Methyl-1H-imidazol-2-yl)-3-{4-[4-methyl-2-(4-trifluoromethyl-phenyl)-thiazol-5-ylmethoxy]-phenyl}-propionic acid; (S)-3-(2-Methyl-2H-1,2,4-triazol-3-yl)-3-{4-[4-methyl-2-(4-trifluoromethyl-phenyl)-thiazol-5-ylmethoxy]-phenyl}-propionic acid; (S)-3-(1-Methyl-1H-tetrazol-5-yl)-3-{4-[4-methyl-2-(4-trifluoromethyl-phenyl)-thiazol-5-ylmethoxy]-phenyl}-propionic acid; (S)-N,N-Dimethyl-3-[4-(4-methyl-2-p-tolyl-thiazol-5-ylmethoxy)-phenyl]-succinamic acid; (S)-3-[4-(4-Methyl-2-p-tolyl-thiazol-5-ylmethoxy)-phenyl]-3-oxazol-2-yl-propionic acid; (S)-3-(1-Methyl-1H-imidazol-2-yl)-3-[4-(4-methyl-2-p-tolyl-thiazol-5-ylmethoxy)-phenyl]-propionic acid; (S)-3-[4-(4-Methyl-2-p-tolyl-thiazol-5-ylmethoxy)-phenyl]-3-(2-methyl-2H-1,2,4-triazol-3-yl)-propionic acid; or (S)-3-(1-Methyl-1H-tetrazol-5-yl)-3-[4-(4-methyl-2-p-tolyl-thiazol-5-ylmethoxy)-phenyl]-propionic acid.

The compounds of the invention include pharmaceutically acceptable salts, solvates, hydrates, tautomers, and/or pro-drugs thereof.

In another aspect, the invention provides pharmaceutical compositions comprising a pharmaceutically acceptable carrier, diluent or excipient and a compound of the invention.

In certain embodiments, the pharmaceutical composition provided comprises a pharmaceutically acceptable carrier, diluent or excipient and a compound selected from the group consisting of (S)-3-[4-(4'-chloro-2'-methyl-biphenyl-3-ylmethoxy)-phenyl]-N,N-dimethyl-succinamic acid; (S)-3-[4-(4'-chloro-2'-methyl-biphenyl-3-ylmethoxy)-phenyl]-3-(1-methyl-1H-imidazol-2-yl)-propionic acid; (S)-3-[4-(4'-chloro-2'-methyl-biphenyl-3-ylmethoxy)-phenyl]-3-(2-methyl-2H-1,2,4-triazol-3-yl)-propionic acid; (S)-3-[4-(4'-chloro-2'-methyl-biphenyl-3-ylmethoxy)-phenyl]-3-(1-methyl-1H-tetrazol-5-yl)-propionic acid; (S)-3-[4-(2'-butoxy-5'-methyl-biphenyl-4-ylmethoxy)-phenyl]-3-(2-methyl-2H-1,2,4-triazol-3-yl)-propionic acid; (S)-N,N-dimethyl-3-[4-(4-methyl-2-p-tolyl-thiazol-5-ylmethoxy)-phenyl]-succinamic acid; and (S)-3-(1-methyl-1H-tetrazol-5-yl)-3-[4-(4-methyl-2-p-tolyl-thiazol-5-ylmethoxy)-phenyl]-propionic acid.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema comprising administering to a subject in need thereof a therapeutically effective amount of a compound of the invention. In some such embodiments, the disease or condition is type II diabetes.

In another aspect, the invention provides the use of the compound for treating or preventing a disease or condition or the use of the compound in the preparation of a medicament or pharmaceutical composition for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. In some such embodiments, the disease or condition is type II diabetes.

In another aspect, the invention provides methods for treating or preventing a disease or condition responsive to the modulation of GPR40 comprising administering to a subject in need thereof a therapeutically effective amount of a compound of the invention.

In yet another aspect, the invention provides the use of the compounds of the invention for treating or preventing a disease or condition or the use of the compounds in the preparation of a medicament or pharmaceutical composition for treating or preventing a disease or condition responsive to the modulation of GPR40.

In another aspect, the invention provides methods for treating or preventing a disease or condition mediated, regulated or influenced by pancreatic β cells comprising administering to a subject in need thereof a therapeutically effective amount of a compound of the invention.

In another aspect, the invention provides the use of the compound, or the use of the compound in the preparation of a medicament or pharmaceutical composition, for treating or preventing a disease or condition mediated, regulated or influenced by pancreatic β cells.

In another aspect, the invention provides methods for modulating GPR40 function in a cell, comprising contacting a cell with a compound of the invention.

In yet another aspect, the invention provides the use of the compound, or the use of the compound in the preparation of a medicament or pharmaceutical composition, for modulating GPR40 function. In some such embodiments, GPR40 function is modulated in a cell.

In another aspect, the invention provides methods for modulating GPR40 function comprising contacting GPR40 with a compound of the invention.

In another aspect, the invention provides methods for modulating circulating insulin concentration in a subject, comprising administering a compound of the invention to the subject. In some such embodiments, the insulin concentration is increased whereas in other embodiments, the insulin concentration is decreased.

In yet another aspect, the invention provides the use of the compound, or the use of the compound in the preparation of a medicament or pharmaceutical composition, for modulating circulating insulin concentration in a subject.

The compounds of the invention may be administered or used in combination with one or more other therapeutic agents. Therefore, in some embodiments, the compounds of the invention are administered or used in combination with a second therapeutic agent. In some such embodiments, the second therapeutic agent is selected from metformin or a thiazolidinedione. The compounds of the invention may be used or administered to a subject before, during, or after the second therapeutic agent.

The compounds, medicaments, and pharmaceutical compositions of the invention may be administered to a subject in various ways. Therefore, in one aspect, a compound or composition of the invention is administered to a subject orally, parenterally, or topically.

Other objects, features and advantages of the invention will become apparent to those skilled in the art from the following description and claims.

5. DETAILED DESCRIPTION OF THE INVENTION

5.1 Abbreviations and Definitions

The term "alkyl", by itself or as part of another substituent, means, unless otherwise stated, a straight or branched chain, or cyclic hydrocarbon radical, or combination thereof, having the number of carbon atoms designated (e.g., $C_1$-$C_4$ means one to four carbons). Examples of alkyl groups include methyl, ethyl, n-propyl, isopropyl, n-butyl, t-butyl, isobutyl, sec-butyl, cyclohexyl, (cyclohexyl)methyl, cyclopropyl, cyclopropylmethyl, homologs and isomers of, for example, n-pentyl, n-hexyl, n-heptyl, n-octyl and the like.

Typically, an alkyl radical will have from zero to three substituents, with those groups having two or fewer substituents being preferred in the present invention. More preferably, an alkyl radical will be unsubstituted or monosubstituted. Most preferably, an alkyl radical will be unsubstituted.

As used herein, the term "GPR40-mediated condition or disorder" and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia and edema.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms).

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

The terms "prevent", "preventing" and "prevention", as used herein, refer to a method of delaying or precluding the onset of a condition or disease and/or its attendant symptoms, barring a subject from acquiring a condition or disease or reducing a subject's risk of acquiring a condition or disease.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "treat", "treating" and "treatment", as used herein, are meant to include alleviating, ameliorating or abrogating a condition or disease and/or its attendant symptoms.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity and the age, weight, etc., of the subject to be treated.

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al., J. Pharm. Sci. 66:1-19 (1977)). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. It should be noted that if the stereochemistry of a structure or a portion of a structure is not indicated with, for example, bold or dashed lines, the structure or portion of the structure is to be interpreted as encompassing all stereoisomers of it.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., J. Jacques et al., Enantiomers, Racemates and Resolutions (Wiley-Interscience, New York 1981); S. H. Wilen et al., Tetrahedron 33:2725 (1997); E. L. Eliel, Stereochemistry of Carbon Compounds (McGraw-Hill, NY 1962); and S. H. Wilen, Tables of Resolving Agents and Optical Resolutions p. 268 (E. L. Eliel, Ed., Univ. of Notre Dame Press, Notre Dame, Ind., 1972).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention.

5.2 Embodiments of the Invention

In one aspect, a class of compounds that modulate GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

5.2.1 Compounds

In one aspect, the present invention provides a compound having formula I:

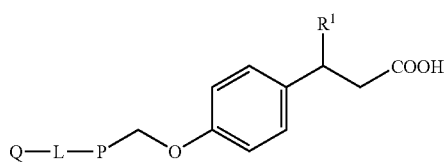

where Q, L, P and R$^1$ are defined below.

Q is an optionally substituted phenyl.

In certain embodiments, Q is a substituted phenyl. In other embodiments, Q is an unsubstituted phenyl.

In some embodiments, Q is a phenyl substituted with one or two substituents independently selected from methyl, trifluoromethyl, halogen, methoxy, ethoxy, butoxy and hydroxyl.

Is some embodiments, Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, 4-methyl-phenyl or unsubstituted phenyl.

L is a bond or O. In some embodiments, L is a bond. In other embodiment L is an O.

In certain embodiments, Q is an unsubstituted phenyl and L is an O.

In some embodiments, Q is a substituted phenyl and L is a bond.

P is a benzene or an optionally substituted thiazole ring.

In certain embodiments, P is a substituted benzene or substituted thiazole. In some embodiments, P is an unsubstituted benzene or unsubstituted thiazole.

In some embodiments, P is an optionally substituted thiazole such as thiazole substituted with a (C$_1$-C$_4$)alkyl group. In some such embodiments, P is a thiazole with a methyl substituent.

R$^1$ is an optionally substituted oxazolyl, imidazolyl, triazolyl, tetrazolyl or —C(O)NR$^2$R$^3$ where R$^2$ and R$^3$ are independently selected from hydrogen and (C$_1$-C$_4$)alkyl.

In certain embodiments, R$^1$ is selected from an optionally substituted imidazolyl or an optionally substituted triazolyl. For example, in some embodiments, R$^1$ is an unsubstituted imidazolyl group or is an unsubstituted triazolyl group whereas in other embodiments, R$^1$ is an imidazolyl or triazolyl group substituted with a (C$_1$-C$_4$)alkyl group. In some embodiments, the imidazolyl or triazolyl is substituted with a methyl group. In some such embodiments, R$^1$ is selected from 1-methyl-1H-imidazol-2-yl or 2-methyl-2H-1,2,4-triazol-3-yl.

In certain embodiments, R$^1$ is selected from an optionally substituted oxazolyl other than 5-methyl-oxazol-2-yl, an optionally substituted tetrazolyl, or —C(O)NR$^2$R$^3$. In some such embodiments, R$^1$ is not dimethylcarbamyl or —C(=O)NH$_2$ when Q is 4-trifluoromethyl-phenyl, P is benzene and L is a bond. In some embodiments, R$^1$ is not an unsubstituted tetrazolyl when Q is 4-trifluoromethyl-phenyl, P is benzene and L is a bond. In some embodiments, R$^1$ is an unsubstituted oxazolyl group or an unsubstituted tetrazolyl group. In other embodiments, R$^1$ is a substituted oxazolyl or tetrazolyl group that is substituted with a (C$_1$-C$_4$)alkyl group. In some such embodiments, R$^1$ is selected from oxazol-2-yl or 1-methyl-1H-tetrazol-5-yl. In other embodiments, R$^1$ is an unsubstituted oxazolyl group or is a methyl substituted tetrazolyl group. In some embodiments, R$^1$ is selected from dimethylcarbamyl, oxazol-2-yl, or 1-methyl-1H-tetrazol-5-yl. In some embodiments, R$^2$ and R$^3$ are both methyl.

The compounds of the invention include pharmaceutically acceptable salts, solvates or prodrugs thereof.

In certain embodiments, ester prodrugs are preferred.

In certain embodiments, the present invention provides a compound of formula I that is a mixture of (S) and (R) enantiomers.

In some embodiments, the compound of formula I is an (S) enantiomer. For example, in some embodiments, the (S) enantiomer can be present in an enantiomeric excess equal to or greater than 90%, 93%, 95% or 97%. In other embodiments, the compound of formula I is an (R) enantiomer. For example, in some embodiments, the (R) enantiomer can be present in an enantiomeric excess equal to or greater than 90%, 93%, 95% or 97%.

In some embodiments, the compound provided has formula Ia or Ib:

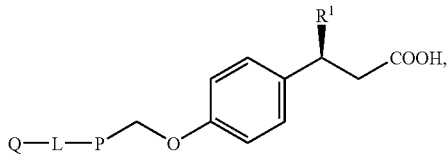

Ia

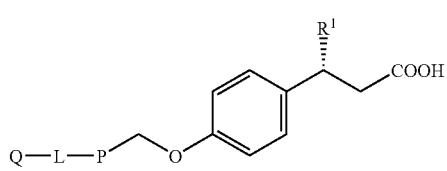

Ib where Q, L, P, and R¹ are defined in formula I above. In some such embodiments, the compound has the formula Ia.

In certain embodiments, the present invention provides a compound having formula II or III:

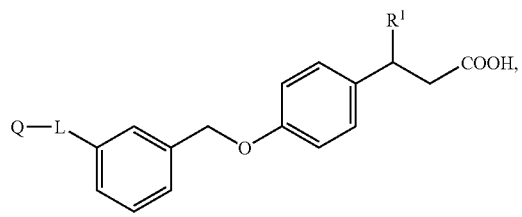

II

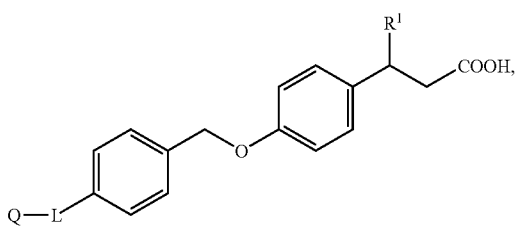

III wherein Q, L and R¹ are as defined above in formula I.

In some embodiments, a compound has the formula IIa or IIIa:

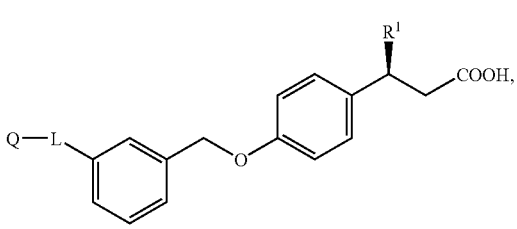

IIa

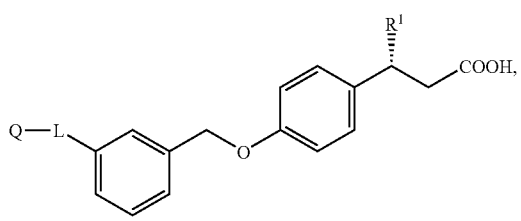

IIIa wherein Q, L and R¹ are as defined above in formula I.

In another embodiment, a compound has the formula IIb or IIIb:

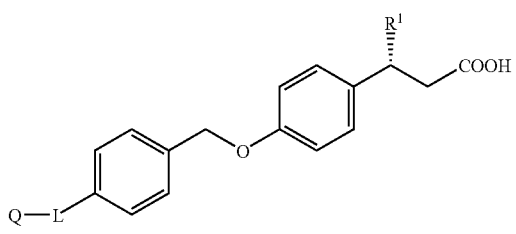

IIb

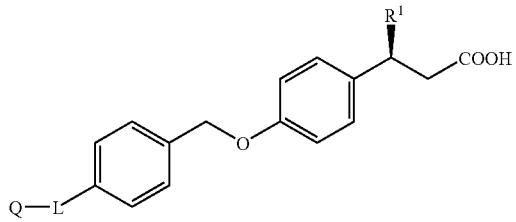

IIIb wherein Q, L and R¹ are as defined above in formula I.

In certain embodiments, the compound is selected from
(S)-N,N-Dimethyl-3-[4-(3-phenoxy-benzyloxy)-phenyl]-succinamic acid,
(S)-3-Oxazol-2-yl-3-[4-(3-phenoxy-benzyloxy)-phenyl]-propionic acid,
(S)-3-(1-Methyl-1H-imidazol-2-yl)-3-[4-(3-phenoxy-benzyloxy)-phenyl]-propionic acid,
(S)-3-(2-Methyl-2H-1,2,4-triazol-3-yl)-3-[4-(3-phenoxy-benzyloxy)-phenyl]-propionic acid, and (S)-3-(1-Methyl-1H-tetrazol-5-yl)-3-[4-(3-phenoxy-benzyloxy)-phenyl]-propionic acid,
or a pharmaceutically acceptable salt or solvate thereof.

In some embodiments, the compound is selected from (S)-3-(1-Methyl-1H-imidazol-2-yl)-3-[4-(3-phenoxy-benzyloxy)-phenyl]-propionic acid, and (S)-3-(2-Methyl-2H-1,2,4-triazol-3-yl)-3-[4-(3-phenoxy-benzyloxy)-phenyl]-propionic acid, or a pharmaceutically acceptable salt or solvate thereof.

In other embodiments, the compound is selected from (S)-N,N-Dimethyl-3-[4-(3-phenoxy-benzyloxy)-phenyl]-succinamic acid, (S)-3-Oxazol-2-yl-3-[4-(3-phenoxy-benzyloxy)-phenyl]-propionic acid, and (S)-3-(1-Methyl-1H-tetrazol-5- yl)-3-[4-(3-phenoxy-benzyloxy)-phenyl]-propionic acid, or a pharmaceutically acceptable salt or solvate thereof.

In some embodiments, the compound is selected from
(S)-N,N-Dimethyl-3-[4-(4-phenoxy-benzyloxy)-phenyl]-succinamic acid,
(S)-3-Oxazol-2-yl-3-[4-(4-phenoxy-benzyloxy)-phenyl]-propionic acid,
(S)-3-(1-Methyl-1H-imidazol-2-yl)-3-[4-(4-phenoxy-benzyloxy)-phenyl]-propionic acid,
(S)-3-(2-Methyl-2H-1,2,4-triazol-3-yl)-3-[4-(4-phenoxy-benzyloxy)-phenyl]-propionic acid, and (S)-3-(1-Methyl-1H-tetrazol-5-yl)-3-[4-(4-phenoxy-benzyloxy)-phenyl]-propionic acid,
or a pharmaceutically acceptable salt or solvate thereof.

In some embodiments, the compound is selected from
(S)-3-(1-Methyl-1H-imidazol-2-yl)-3-[4-(4-phenoxy-benzyloxy)-phenyl]-propionic acid and (S)-3-(2-Methyl-2H-1,2,4-triazol-3-yl)-3-[4-(4-phenoxy-benzyloxy)-phenyl]-propionic acid, or a pharmaceutically acceptable salt or solvate thereof.

In some embodiments, the compound is selected from
(S)-3-(1-Methyl-1H-imidazol-2-yl)-3-[4-(3-phenoxy-benzyloxy)-phenyl]-propionic acid;
(S)-3-(2-Methyl-2H-1,2,4-triazol-3-yl)-3-[4-(3-phenoxy-benzyloxy)-phenyl]-propionic acid;
(S)-3-(1-Methyl-1H-imidazol-2-yl)-3-[4-(4-phenoxy-benzyloxy)-phenyl]-propionic acid; and
(S)-3-(2-Methyl-2H-1,2,4-triazol-3-yl)-3-[4-(4-phenoxy-benzyloxy)-phenyl]-propionic acid; or a pharmaceutically acceptable salt or solvate thereof.

In some embodiments, the compound is selected from
(S)-N,N-Dimethyl-3-[4-(4-phenoxy-benzyloxy)-phenyl]-succinamic acid,
(S)-3-Oxazol-2-yl-3-[4-(4-phenoxy-benzyloxy)-phenyl]-propionic acid, and
(S)-3-(1-Methyl-1H-tetrazol-5-yl)-3-[4-(4-phenoxy-benzyloxy)-phenyl]-propionic acid,
or a pharmaceutically acceptable salt or solvate thereof.

In some embodiments, the compound is selected from
(S)-N,N-Dimethyl-3-[4-(3-phenoxy-benzyloxy)-phenyl]-succinamic acid;
(S)-3-Oxazol-2-yl-3-[4-(3-phenoxy-benzyloxy)-phenyl]-propionic acid;
(S)-3-(1-Methyl-1H-tetrazol-5-yl)-3-[4-(3-phenoxy-benzyloxy)-phenyl]-propionic acid;
(S)-N,N-Dimethyl-3-[4-(4-phenoxy-benzyloxy)-phenyl]-succinamic acid;
(S)-3-Oxazol-2-yl-3-[4-(4-phenoxy-benzyloxy)-phenyl]-propionic acid; and
(S)-3-(1-Methyl-1H-tetrazol-5-yl)-3-[4-(4-phenoxy-benzyloxy)-phenyl]-propionic acid; or a pharmaceutically acceptable salt or solvate thereof.

In some embodiments, the compound is selected from
(S)-3-Oxazol-2-yl-3-[4-(4'-trifluoromethyl-biphenyl-3-ylmethoxy)-phenyl]-propionic acid,
(S)-3-(1-Methyl-1H-imidazol-2-yl)-3-[4-(4'-trifluoromethyl-biphenyl-3-ylmethoxy)-phenyl]-propionic acid,
(S)-3-(2-Methyl-2H-1,2,4-triazol-3-yl)-3-[4-(4'-trifluoromethyl-biphenyl-3-ylmethoxy)-phenyl]-propionic acid,
(S)-3-(1-Methyl-1H-tetrazol-5-yl)-3-[4-(4'-trifluoromethyl-biphenyl-3-ylmethoxy)-phenyl]-propionic acid,
(S)-3-[4-(3'-Chloro-2'-methyl-biphenyl-3-ylmethoxy)-phenyl]-N,N-dimethyl-succinamic acid,
(S)-3-[4-(3'-Chloro-2'-methyl-biphenyl-3-ylmethoxy)-phenyl]-3-oxazol-2-yl-propionic acid,
(S)-3-[4-(3'-Chloro-2'-methyl-biphenyl-3-ylmethoxy)-phenyl]-3-(1-methyl-1H-imidazol-2-yl)-propionic acid,
(S)-3-[4-(3'-Chloro-2'-methyl-biphenyl-3-ylmethoxy)-phenyl]-3-(2-methyl-2H-1,2,4-triazol-3-yl)-propionic acid,
(S)-3-[4-(3'-Chloro-2'-methyl-biphenyl-3-ylmethoxy)-phenyl]-3-(1-methyl-1H-tetrazol-5-yl)-propionic acid,
(S)-3-[4-(4'-Chloro-2'-methyl-biphenyl-3-ylmethoxy)-phenyl]-N,N-dimethyl-succinamic acid,
(S)-3-[4-(4'-Chloro-2'-methyl-biphenyl-3-ylmethoxy)-phenyl]-3-oxazol-2-yl-propionic acid,
(S)-3-[4-(4'-Chloro-2'-methyl-biphenyl-3-ylmethoxy)-phenyl]-3-(1-methyl-1H-imidazol-2-yl)-propionic acid,
(S)-3-[4-(4'-Chloro-2'-methyl-biphenyl-3-ylmethoxy)-phenyl]-3-(2-methyl-2H-1,2,4-triazol-3-yl)-propionic acid,
(S)-3-[4-(4'-Chloro-2'-methyl-biphenyl-3-ylmethoxy)-phenyl]-3-(1-methyl-1H-tetrazol-5-yl)-propionic acid,
(S)-3-[4-(5'-Chloro-2'-methyl-biphenyl-3-ylmethoxy)-phenyl]-N,N-dimethyl-succinamic acid,
(S)-3-[4-(5'-Chloro-2'-methyl-biphenyl-3-ylmethoxy)-phenyl]-3-oxazol-2-yl-propionic acid,
(S)-3-[4-(5'-Chloro-2'-methyl-biphenyl-3-ylmethoxy)-phenyl]-3-(1-methyl-1H-imidazol-2-yl)-propionic acid,
(S)-3-[4-(5'-Chloro-2'-methyl-biphenyl-3-ylmethoxy)-phenyl]-3-(2-methyl-2H-1,2,4-triazol-3-yl)-propionic acid,
(S)-3-[4-(5'-Chloro-2'-methyl-biphenyl-3-ylmethoxy)-phenyl]-3-(1-methyl-1H-tetrazol-5-yl)-propionic acid,
(S)-3-[4-(2'-Butoxy-5'-methyl-biphenyl-4-ylmethoxy)-phenyl]-N,N-dimethyl-succinamic acid,
(S)-3-[4-(2'-Butoxy-5'-methyl-biphenyl-4-ylmethoxy)-phenyl]-3-oxazol-2-yl-propionic acid,
(S)-3-[4-(2'-Butoxy-5'-methyl-biphenyl-4-ylmethoxy)-phenyl]-3-(1-methyl-1H-imidazol-2-yl)-propionic acid,
(S)-3-[4-(2'-Butoxy-5'-methyl-biphenyl-4-ylmethoxy)-phenyl]-3-(2-methyl-2H-1,2,4-triazol-3-yl)-propionic acid,
(S)-3-[4-(2'-Butoxy-5'-methyl-biphenyl-4-ylmethoxy)-phenyl]-3-(1-methyl-1H-tetrazol-5-yl)-propionic acid,
(S)-3-[4-(3'-Ethoxy-biphenyl-4-ylmethoxy)-phenyl]-N,N-dimethyl-succinamic acid,
(S)-3-[4-(3'-Ethoxy-biphenyl-4-ylmethoxy)-phenyl]-3-oxazol-2-yl-propionic acid,
(S)-3-[4-(3'-Ethoxy-biphenyl-4-ylmethoxy)-phenyl]-3-(1-methyl-1H-imidazol-2-yl)-propionic acid,
(S)-3-[4-(3'-Ethoxy-biphenyl-4-ylmethoxy)-phenyl]-3-(2-methyl-2H-1,2,4-triazol-3-yl)-propionic acid, and
(S)-3-[4-(3'-Ethoxy-biphenyl-4-ylmethoxy)-phenyl]-3-(1-methyl-1H-tetrazol-5-yl)-propionic acid,
or a pharmaceutically acceptable salt or solvate thereof.

In some embodiments, the compound is selected from
(S)-3-(1-Methyl-1H-imidazol-2-yl)-3-[4-(4'-trifluoromethyl-biphenyl-3-ylmethoxy)-phenyl]-propionic acid,
(S)-3-(2-Methyl-2H-1,2,4-triazol-3-yl)-3-[4-(4'-trifluoromethyl-biphenyl-3-ylmethoxy)-phenyl]-propionic acid,
(S)-3-[4-(3'-Chloro-2'-methyl-biphenyl-3-ylmethoxy)-phenyl]-3-(1-methyl-1H-imidazol-2-yl)-propionic acid,
(S)-3-[4-(3'-Chloro-2'-methyl-biphenyl-3-ylmethoxy)-phenyl]-3-(2-methyl-2H-1,2,4-triazol-3-yl)-propionic acid,
(S)-3-[4-(4'-Chloro-2'-methyl-biphenyl-3-ylmethoxy)-phenyl]-3-(1-methyl-1H-imidazol-2-yl)-propionic acid,
(S)-3-[4-(4'-Chloro-2'-methyl-biphenyl-3-ylmethoxy)-phenyl]-3-(2-methyl-2H-1,2,4-triazol-3-yl)-propionic acid,
(S)-3-[4-(5'-Chloro-2'-methyl-biphenyl-3-ylmethoxy)-phenyl]-3-(1-methyl-1H-imidazol-2-yl)-propionic acid,
(S)-3-[4-(5'-Chloro-2'-methyl-biphenyl-3-ylmethoxy)-phenyl]-3-(2-methyl-2H-1,2,4-triazol-3-yl)-propionic acid,
(S)-3-[4-(2'-Butoxy-5'-methyl-biphenyl-4-ylmethoxy)-phenyl]-3-(1-methyl-1H-imidazol-2-yl)-propionic acid,
(S)-3-[4-(2'-Butoxy-5'-methyl-biphenyl-4-ylmethoxy)-phenyl]-3-(2-methyl-2H-1,2,4-triazol-3-yl)-propionic acid, (S)-3-[4-(3'-Ethoxy-biphenyl-4-ylmethoxy)-phenyl]-3-(1-methyl-1H-imidazol-2-yl)-propionic acid, and (S)-3-[4-(3'-Ethoxy-biphenyl-4-ylmethoxy)-phenyl]-3-(2-methyl-2H-1,2,4-triazol-3-yl)-propionic acid, or a pharmaceutically acceptable salt or solvate thereof.

In some embodiments, the compound is selected from (S)-3-Oxazol-2-yl-3-[4-(4'-trifluoromethyl-biphenyl-3-yl-methoxy)-phenyl]-propionic acid, (S)-3-(1-Methyl-1H-tetrazol-5-yl)-3-[4-(4'-trifluoromethyl-biphenyl-3-ylmethoxy)-phenyl]-propionic acid, (S)-3-[4-(3'-Chloro-2'-methyl-biphenyl-3-ylmethoxy)-phenyl]-N,N-dimethyl-succinamic acid, (S)-3-[4-(3'-Chloro-2'-methyl-biphenyl-3-ylmethoxy)-phenyl]-3-oxazol-2-yl-propionic acid, (S)-3-[4-(3'-Chloro-2'-methyl-biphenyl-3-ylmethoxy)-phenyl]-3-(1-methyl-1H-tetrazol-5-yl)-propionic acid, (S)-3-[4-(4'-Chloro-2'-methyl-biphenyl-3-ylmethoxy)-phenyl]-N,N-dimethyl-succinamic acid, (S)-3-[4-(4'-Chloro-2'-methyl-biphenyl-3-ylmethoxy)-phenyl]-3-oxazol-2-yl-propionic acid, (S)-3-[4-(4'-Chloro-2'-methyl-biphenyl-3-ylmethoxy)-phenyl]-3-(1-methyl-1H-tetrazol-5-yl)-propionic acid, (S)-3-[4-(5'-Chloro-2'-methyl-biphenyl-3-ylmethoxy)-phenyl]-N,N-dimethyl-succinamic acid, (S)-3-[4-(5'-Chloro-2'-methyl-biphenyl-3-ylmethoxy)-phenyl]-3-oxazol-2-yl-propionic acid, (S)-3-[4-(5'-Chloro-2'-methyl-biphenyl-3-ylmethoxy)-phenyl]-3-(1-methyl-1H-tetrazol-5-yl)-propionic acid, (S)-3-[4-(2'-Butoxy-5'-methyl-biphenyl-4-ylmethoxy)-phenyl]-N,N-dimethyl-succinamic acid, (S)-3-[4-(2'-Butoxy-5'-methyl-biphenyl-4-ylmethoxy)-phenyl]-3-oxazol-2-yl-propionic acid, (S)-3-[4-(2'-Butoxy-5'-methyl-biphenyl-4-ylmethoxy)-phenyl]-3-(1-methyl-1H-tetrazol-5-yl)-propionic acid, (S)-3-[4-(3'-Ethoxy-biphenyl-4-ylmethoxy)-phenyl]-N,N-dimethyl-succinamic acid, (S)-3-[4-(3'-Ethoxy-biphenyl-4-ylmethoxy)-phenyl]-3-oxazol-2-yl-propionic acid, and (S)-3-[4-(3'-Ethoxy-biphenyl-4-ylmethoxy)-phenyl]-3-(1-methyl-1H-tetrazol-5-yl)-propionic acid, or a pharmaceutically acceptable salt or solvate thereof.

In certain embodiments, the compound of the invention has formula IV:

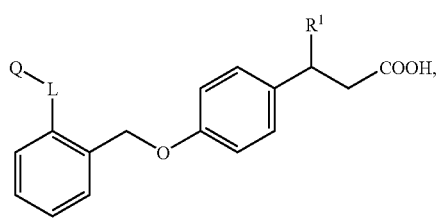

IV wherein Q, L and $R^1$ are as defined in formula I above.

In certain embodiments, the present invention provides a compound having formula V:

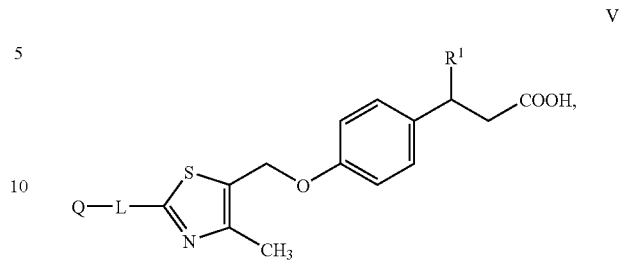

V wherein Q, L and $R^1$ are defined in formula I above.

In some embodiments, the compound provided has formula Va or Vb:

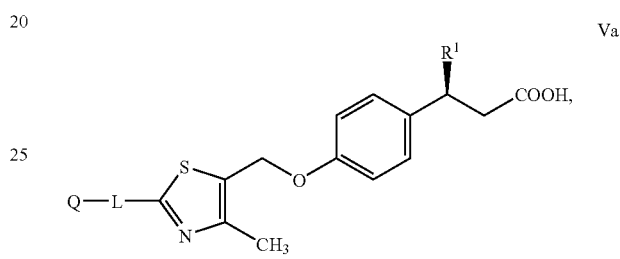

Va

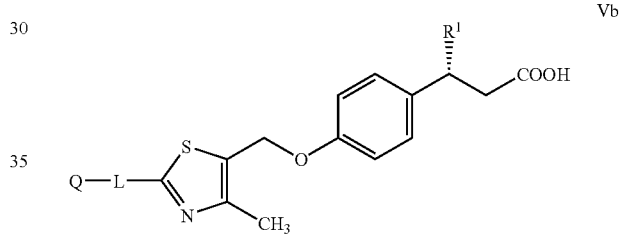

Vb wherein Q, L and $R^1$ are defined in formula I above. In some embodiments, the compound has the formula Va.

In certain embodiments, the compound is selected from (S)-N,N-Dimethyl-3-{4-[4-methyl-2-(4-trifluoromethyl-phenyl)-thiazol-5-ylmethoxy]-phenyl}-succinamic acid;

(S)-3-{4-[4-Methyl-2-(4-trifluoromethyl-phenyl)-thiazol-5-ylmethoxy]-phenyl}-3-oxazol-2-yl-propionic acid;

(S)-3-(1-Methyl-1H-imidazol-2-yl)-3-{4-[4-methyl-2-(4-trifluoromethyl-phenyl)-thiazol-5-ylmethoxy]-phenyl}-propionic acid;

(S)-3-(2-Methyl-2H-1,2,4-triazol-3-yl)-3-{4-[4-methyl-2-(4-trifluoromethyl-phenyl)-thiazol-5-ylmethoxy]-phenyl}-propionic acid;

(S)-3-(1-Methyl-1H-tetrazol-5-yl)-3-{4-[4-methyl-2-(4-trifluoromethyl-phenyl)-thiazol-5-ylmethoxy]-phenyl}-propionic acid;

(S)-N,N-Dimethyl-3-[4-(4-methyl-2-p-tolyl-thiazol-5-ylmethoxy)-phenyl]-succinamic acid;

(S)-3-[4-(4-Methyl-2-p-tolyl-thiazol-5-ylmethoxy)-phenyl]-3-oxazol-2-yl-propionic acid;

(S)-3-(1-Methyl-1H-imidazol-2-yl)-3-[4-(4-methyl-2-p-tolyl-thiazol-5-ylmethoxy)-phenyl]-propionic acid;

(S)-3-[4-(4-Methyl-2-p-tolyl-thiazol-5-ylmethoxy)-phenyl]-3-(2-methyl-2H-1,2,4triazol-3-yl)-propionic acid; and (S)-3-(1-Methyl-1H-tetrazol-5-yl)-3-[4-(4-methyl-2-p-tolyl-thiazol-5-ylmethoxy)-phenyl]-propionic acid; or a pharmaceutically acceptable salt or solvate thereof.

In certain embodiments, the compound is selected from (S)-3-(1-Methyl-1H-imidazol-2-yl)-3-{4-[4-methyl-2-(4-trifluoromethyl-phenyl)-thiazol-5-ylmethoxy]-phenyl}-propionic acid;

(S)-3-(2-Methyl-2H-1,2,4-triazol-3-yl)-3-{4-[4-methyl-2-(4-trifluoromethyl-phenyl)-thiazol-5-ylmethoxy]-phenyl}-propionic acid;

(S)-3-(1-Methyl-1H-imidazol-2-yl)-3-[4-(4-methyl-2-p-tolyl-thiazol-5-ylmethoxy)-phenyl]-propionic acid; and (S)-3-[4-(4-Methyl-2-p-tolyl-thiazol-5-ylmethoxy)-phenyl]-3-(2-methyl-2H-1,2,4-triazol-3-yl)-propionic acid; or a pharmaceutically acceptable salt or solvate thereof.

In certain embodiments, the compound is selected from (S)-N,N-Dimethyl-3-{4-[4-methyl-2-(4-trifluoromethyl-phenyl)-thiazol-5-ylmethoxy]-phenyl}-succinamic acid;

(S)-3-{4-[4-Methyl-2-(4-trifluoromethyl-phenyl)-thiazol-5-ylmethoxy]-phenyl}-3-oxazol-2-yl-propionic acid;

(S)-3-(1-Methyl-1H-tetrazol-5-yl)-3-{4-[4-methyl-2-(4-trifluoromethyl-phenyl)-thiazol-5-ylmethoxy]-phenyl}-propionic acid;

(S)-N,N-Dimethyl-3-[4-(4-methyl-2-p-tolyl-thiazol-5-ylmethoxy)-phenyl]-succinamic acid;

(S)-3-[4-(4-Methyl-2-p-tolyl-thiazol-5-ylmethoxy)-phenyl]-3-oxazol-2-yl-propionic acid; and (S)-3-(1-Methyl-1H-tetrazol-5-yl)-3-[4-(4-methyl-2-p-tolyl-thiazol-5-ylmethoxy)-phenyl]-propionic acid; or a pharmaceutically acceptable salt or solvate thereof.

5.2.2 Preparation of the Compounds

The compounds of the invention can be prepared using a variety of synthetic or semisynthetic techniques. The examples in Section 6 below provide a variety of synthesis routes to the compounds provided herein. A general scheme for preparation of compounds of formula I is presented in Scheme 1. Conditions for synthesizing the intermediate ester and converting it to a carboxylic acid are found throughout the examples herein. Appropriate starting materials can be prepared by techniques known or apparent to those of skill in the art or the starting materials may be commercially available.

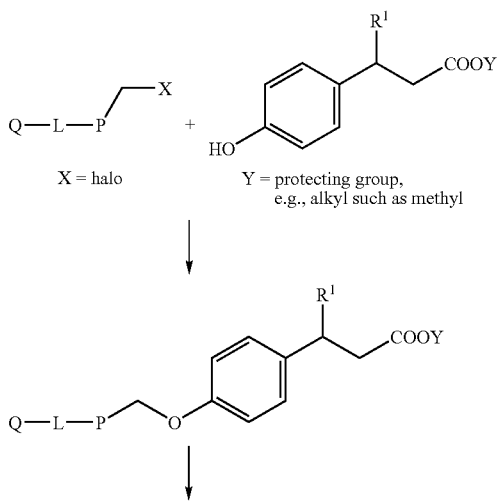

Scheme 1

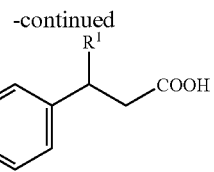

-continued

One of skill in the art will understand that the synthetic routes can be modified to use different starting materials or alternative reagents and that suitable adjustments in conditions (e.g., temperatures, solvents, etc.) can be made to accomplish the desired transformations. Additionally, one of skill in the art will recognize that protecting groups may be necessary for the preparation of certain compounds and will be aware of those conditions compatible with a selected protecting group. Suitable protecting groups are known to those skilled in the art. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof.

5.2.3 Compositions

In another aspect, the invention provides pharmaceutical compositions suitable for pharmaceutical use comprising one or more compounds of the invention and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

In certain embodiments, the present invention provides a pharmaceutical composition comprising a compound of formula I, Ia, Ib, II, Ia, IIb, III, IIIa, IIIb, IV, V, Va or Vb.

In some embodiments, the pharmaceutical composition comprises a compound selected from the group consisting of (S)-3-[4-(4'-Chloro-2'-methyl-biphenyl-3-ylmethoxy)-phenyl]-N,N-dimethyl-succinamic acid;

(S)-3-[4-(4'-Chloro-2'-methyl-biphenyl-3-ylmethoxy)-phenyl]-3-(1-methyl-1H-imidazol-2-yl)-propionic acid;

(S)-3-[4-(4'-Chloro-2'-methyl-biphenyl-3-ylmethoxy)-phenyl]-3-(2-methyl-2H-1,2,4-triazol-3-yl)-propionic acid;

(S)-3-[4-(4'-Chloro-2'-methyl-biphenyl-3-ylmethoxy)-phenyl]-3-(1-methyl-1H-tetrazol-5-yl)-propionic acid;

(S)-3-[4-(2'-Butoxy-5'-methyl-biphenyl-4-ylmethoxy)-phenyl]-3-(2-methyl-2H-1,2,4-triazol-3-yl)-propionic acid;

(S)-N,N-Dimethyl-3-[4-(4-methyl-2-p-tolyl-thiazol-5-ylmethoxy)-phenyl]-succinamic acid; and (S)-3-(1-Methyl-1H-tetrazol-5-yl)-3-[4-(4-methyl-2-p-tolyl-thiazol-5-ylmethoxy)-phenyl]-propionic acid or a pharmaceutically acceptable salt or solvate thereof.

In some embodiments, the pharmaceutical composition comprises a compound selected from the group consisting of (S)-3-[4-(4'-Chloro-2'-methyl-biphenyl-3-ylmethoxy)-phenyl]-3-(1-methyl-1H-imidazol-2-yl)-propionic acid;

(S)-3-[4-(4'-Chloro-2'-methyl-biphenyl-3-ylmethoxy)-phenyl]-3-(2-methyl-2H-1,2,4-triazol-3-yl)-propionic acid; and (S)-3-[4-(2'-Butoxy-5'-methyl-biphenyl-4-ylmethoxy)-phenyl]-3-(2-methyl-2H-1,2,4-triazol-3-yl)-propionic acid;

or a pharmaceutically acceptable salt or solvate thereof.

In some embodiments, the pharmaceutical composition comprises a compound selected from the group consisting of (S)-3-[4-(4'-Chloro-2'-methyl-biphenyl-3-ylmethoxy)-phenyl]-N,N-dimethyl-succinamic acid;

(S)-3-[4-(4'-Chloro-2'-methyl-biphenyl-3-ylmethoxy)-phenyl]-3-(1-methyl-1H-tetrazol-5-yl)-propionic acid;

(S)-N,N-Dimethyl-3-[4-(4-methyl-2-p-tolyl-thiazol-5-ylmethoxy)-phenyl]-succinamic acid; and (S)-3-(1-Methyl-1H-tetrazol-5-yl)-3-[4-(4-methyl-2-p-tolyl-thiazol-5-ylmethoxy)-phenyl]-propionic acid or a pharmaceutically acceptable salt or solvate thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. As used herein, topical application is also meant to include the use of mouthwashes and gargles.

In addition to the excipients and carriers described above, pharmaceutically acceptable excipients and carriers known to those skilled in the art may be used to prepare compositions using the compounds of the present invention. Such excipients and carriers are described, for example, in "Remingtons Pharmaceutical Sciences" Mack Pub. Co., New Jersey (1991) and other related such texts.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

5.2.4 Methods of Use and Uses

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such methods include administering a therapeutically effective amount of a compound or composition of the invention to a subject in need thereof.

In one embodiment, the disease or condition is type II diabetes.

In another aspect, the invention provides the use of the compound or compositions for treating or preventing a disease or condition and the use of the compound in the preparation of a medicament or pharmaceutical composition for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. In some such embodiments, the disease or condition is type II diabetes.

In another aspect, the present invention provides a method for treating a disease or condition responsive to the modulation of GPR40. Such methods include administering a therapeutically effective amount of a compound or composition of the invention to a subject in need thereof.

In yet another aspect, the invention provides the use of the compounds of the invention for treating or preventing a disease or condition or the use of the compounds in the preparation of a medicament or pharmaceutical composition for treating or preventing a disease or condition responsive to the modulation of GPR40.

In some embodiments, the disease or condition responsive to the modulation of GPR40 is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hyptertension.

In some embodiments of administering the compound or composition of the invention, the compound or composition is administered orally.

In other embodiments, the compound or composition is administered parenterally.

In other embodiments, the compound or composition is administered in combination with a second therapeutic agent. The second therapeutic agent may be administered before, during, or after the compound or composition of the invention is administered.

In some embodiments, the second therapeutic agent is an insulin sensitizing agent, such as, for example, metformin or a thiazolidinedione.

In another aspect, the invention provides methods for treating or preventing a disease or condition mediated, regulated or influenced by pancreatic β cells. Such methods include administering a therapeutically effective amount of a compound of the invention to a subject in need thereof.

In another aspect, the invention provides the use of the compound, or the use of the compound in the preparation of a medicament or pharmaceutical composition, for treating or preventing a disease or condition mediated, regulated or influenced by pancreatic β cells.

In another aspect, the invention provides methods of treating or preventing a disease or disorder responsive to modulation of GPR40. Such methods include administering a therapeutically effective amount of one or more of the subject compounds or compositions to a subject having such a disease or disorder.

In yet another aspect, the invention provides methods of treating or preventing a GPR40-mediated condition, disease or disorder. Such methods include administering a therapeutically effective amount of one or more of the subject compounds or compositions to a subject having such a condition, disease or disorder.

In yet another aspect, the invention provides methods of modulating GPR40. Such methods include contacting a cell with one or more of the subject compounds or compositions. Therefore, in some embodiments, the invention provides the use of the compound, or the use of the compound in the preparation of a medicament or pharmaceutical composition, for modulating GPR40 function. In some such embodiments, GPR40 function is modulated in a cell.

In some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefor, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition modulated by GPR40. In some embodiments, therapeutic compositions are provided that include a compound of the invention and a second therapeutic agent as a combined preparation for simultaneous, separate or sequential use in the prophylactic treatment of a subject at risk for a disease or condition modulated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (Glucophage®), α-glucosidase inhibitors (acarbose), insulin sensitizers, e.g., thiazolidinone compounds, rosiglitazone (Avandia®), troglitazone (Rezulin®), ciglitazone, pioglitazone (Actos®) and englitazone, DPP-IV inhibitors, e.g., vildagliptin (Galvus®), sitagliptin (Januvia™), and GLP-I analogs, e.g., exenatide (Byetta®). In some embodiments, a compound of the invention may be administered along with a DPP-IV inhibitor or a GLP-I analog.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject. Such methods include administering a therapeutically effective amount of a compound or composition of the invention to the subject.

In some embodiments, the insulin concentration is increased.

In other embodiments, the insulin concentration is decreased.

In yet another aspect, the invention provides the use of the compound, or the use of the compound in the preparation of a medicament or pharmaceutical composition, for modulating circulating insulin concentration in a subject. In some such embodiments, the insulin concentration is increased whereas in other embodiments the insulin concentration is decreased after such a medicament is administered to a subject.

The following examples are offered by way of illustration and are not intended to limit the scope of the invention. Those of skill in the art will readily recognize a variety of noncritical parameters that could be modified to yield essentially similar results.

6. EXAMPLES

The following examples are offered by way of illustration and are not intended to limit the scope of the invention. Those of skill in the art will readily recognize a variety of noncritical parameters that could be modified to yield essentially similar results.

Unless otherwise stated, all compounds were obtained from commercial sources or were prepared using the methods and experimental procedures described herein. Various procedures are also set forth in published U.S. patent application No. 2006/0004012. The following abbreviations are used to refer to various reagents, solvents, experimental procedures, or analytical techniques that are described in the examples:

| | |
|---|---|
| DCM | Dichloromethane |
| DMF | N,N-Dimethyl Formamide |
| DMSO | Dimethyl Sulfoxide |
| ESI | Electrospray Ionization |
| EtOAc | Ethyl Acetate |
| EtOH | Ethanol |
| HPLC | High Performance Liquid Chromatography |
| MeOH | Methanol |
| MS | Mass Spectrometry |
| NMR | Nuclear Magnetic Resonance |
| i-PrOH | i-Propanol |
| n-PrOH | n-Propanol |
| PCC | Pyridinium Chlorochromate |
| t-BuOH | t-Butanol |
| THF | Tetrahydrofuran |
| TFA | Trifluoroacetic Acid |

6.1 Example 1

This example illustrates the preparation of (3S)-3-(4-hydroxy-phenyl)-hex-4-ynoic acid methyl ester (1).

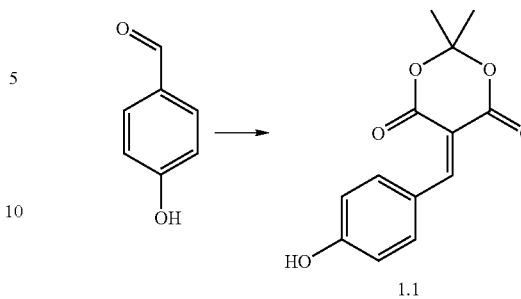

1.1

5-(4-Hydroxy-benzylidene)-2,2-dimethyl-[1,3]dioxane-4,6-dione (1.1). Condensation with Meldrum's acid is carried out according to the method of Bigi et al., Tetrahedron Lett. 42:5203-5205 (2001). A 2L pear-shaped flask was charged with 4-hydroxybenzaldehyde (50 g, 409 mmol) and water (400 mL). The flask was placed in a water bath at 75° C. and Meldrum's acid (62 g, 430 mmol) was added as a slurry in 400 mL of water. The reaction mixture was agitated for 2 hours and cooled in an ice bath for 2 hours. The product was collected by filtration and rinsed with cold water. After drying thoroughly, 95 g of adduct 1.1 was obtained as a fine yellow powder. $^1$H NMR (500 MHz, DMSO-$d_6$) δ 9.75 (br s, 1H); 8.27 (s, 1H); 8.24 (d, 2H, J=10 Hz); 6.98 (d, 2H, J=10 Hz); 1.76 (s, 6H). MS ESI (pos.) m/e: 519.0 (2M+Na).

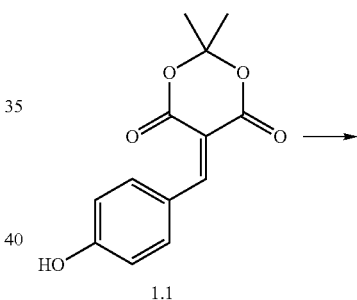

1.1

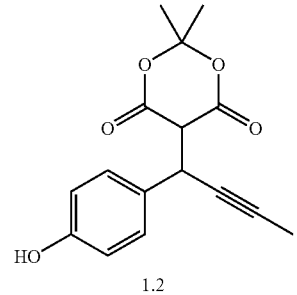

1.2

(+/−)-5-[1-(4-Hydroxy-phenyl)-but-2-ynyl]-2,2-dimethyl-[1,3]dioxane-4,6-dione (1.2). An oven-dried 3L 3-neck flask equipped with a mechanical stirrer, nitrogen inlet and nitrogen outlet was placed in a room-temperature water bath. After purging with nitrogen for 20 minutes, a solution of 1-propynylmagnesium bromide in THF (0.5 N, 600 mL) was added by cannula. In a separate oven-dried and nitrogen-flushed 500 mL round bottom flask, compound 1.1 (35 g, 142 mmol) was dissolved in anhydrous THF (350 mL) with gentle warming. The solution of 1.1 was added over 15 minutes. Over the course of the addition, the reaction mixture changed to a thick, yellow suspension. After the addition was complete, the reaction mixture was stirred for 15 minutes and quenched with aqueous NH₄Cl (0.6 N, 750 mL) and diluted with hexanes (800 mL). The layers were separated and the organic layer discarded. The aqueous layer was acidified to pH ~2 with saturated aqueous KHSO4 and extracted with EtOAc (2×400 mL). The combined extracts were washed with saturated brine, dried over MgSO₄, filtered, and concentrated to a light yellow solid (37 g). ¹H NMR (500 MHz, acetone-d₆) δ 8.26 (s, 1H); 7.39 (d, 2H, J=8.5 Hz); 6.76 (d, 2H, J=8.4 Hz); 4.73 (br s, 1H); 4.46 (d, 1H, J=2.4 Hz); 1.82 (s, 3H); 1.81 (s, 3H); 1.64 (s, 3H). MS ESI (pos.) m/e: 599.0 (2M+Na).

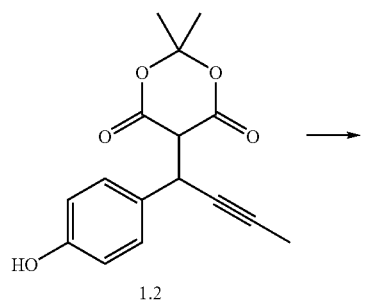

1.2

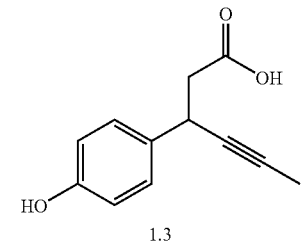

1.3

(+/−)-3-(4-Hydroxy-phenyl)-hex-4-ynoic acid (1.3). A 1 L round bottom flask was charged with compound 1.2 (37 g), diethyl ketone (160 mL), and water (80 mL). The suspension was heated to reflux for 48 hours. After cooling, the aqueous layer was saturated with NaCl(s) and separated. The organic layer was dried over MgSO₄, filtered, and concentrated to a light brown oil which was crystallized from hot EtOAc:hexanes (1:2). After collecting and drying, the product was obtained as an off-white powder (20.3 g). ¹H NMR (500 MHz, DMSO-d₆) δ 12.2 (s, 1H); 9.27 (s, 1H); 7.12 (d, 2H, J=8.5 Hz); 6.67 (d, 2H, J=8.6 Hz); 3.87 (m, 1H); 2.54 (m, 2H); 1.82 (d, 3H, J=2.4 Hz). MS ESI (pos.) m/e: 205.1 (M+H); 227.1 (M+Na).

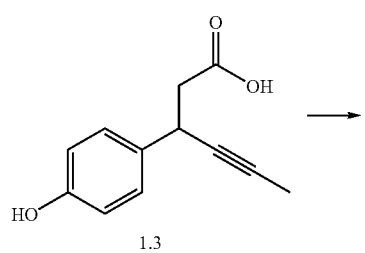

1.3

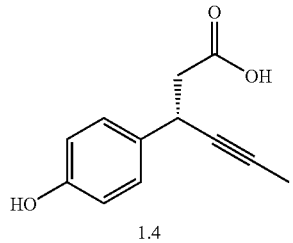

1.4

(3S)-3-(4-Hydroxy-phenyl)-hex-4-ynoic acid (1.4). A 5 L round bottom flask was charged with compound 1.3 (66.4 g, 325 mmol) and i-PrOH (1 L) and heated to 70° C. (1S, 2R)-1-amino-2-indanol (46.1 g, 309 mmol) was dissolved in i-PrOH (1 L) with gentle warming. The solution of amine was added to the dissolved carboxylic acid and the resulting solution was allowed to cool to room temperature. After 16 hours, the crystals were collected and dried. The salt was re-suspended in 2 L of i-PrOH and dissolved by heating to reflux. After allowing to cool to room temperature, the salt was collected after 16 hours. A small sample of the salt was decomposed with aqueous acid and the free carboxylic acid was analyzed by chiral HPLC (Daicel ChiralPAK AD-H column, eluant: 0.1% TFA in 90:10 hexanes:i-PrOH) and was found to have 75% ee. The salt was re-suspended in 1.5 L of i-PrOH and dissolved by heating to reflux. After allowing to cool to room temperature, the salt was collected after 16 hours. This material was found to have 96% ee by chiral HPLC. This material was suspended in EtOAc (300 mL) and water (100 mL). Saturated aqueous KHSO₄ (100 mL) was added with vigorous mixing. After two clear layers were obtained, the layers were separated, and the aqueous layer was extracted with EtOAc (100 mL). The combined extracts were washed with saturated brine, dried over MgSO₄, filtered, and concentrated to a light yellow oil which crystallized on drying in vacuo. Compound 1.4 was obtained as an off-white solid (23.5 g).

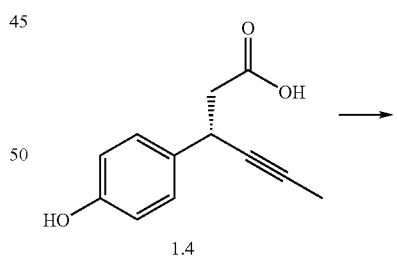

1.4

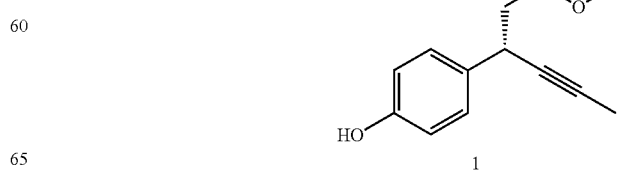

1

(3S)-3-(4-Hydroxy-phenyl)-hex-4-ynoic acid methyl ester (1). Phenol 1.4 (23.5 g, 115 mmol) was dissolved in acetone (230 mL) and treated with $KHCO_3$ (11.5 g, 115 mmol). After 15 minutes, methyl iodide (5 mL, 80 mmol) was added, and the reaction stirred at 40° C. for 14 hours. An additional portion of methyl iodide (3 mL, 48 mmol) was added, and heating was continued for 24 hours. Potassium salts were removed by filtration and thoroughly rinsed with acetone. The filtrate was concentrated to an oil which was filtered through a 1 cm plug of silica gel. Elution with 2.5% MeOH in DCM followed by concentration provided phenol 1 (21.5 g) as a light yellow oil. $^1H$ NMR (500 MHz, acetone-$d_6$) δ 8.2 (br s, 1H); 7.20 (d, 2H, J=9.5 Hz); 6.77 (d, 2H, J=9.0 Hz); 3.98 (m, 1H); 3.60 (s, 3H); 2.65 (m, 2H); 1.78 (d, 3H, J=2.5 Hz). MS ESI (pos.) m/e: 219.1 (M+H); 241.1 (M+Na).

6.2 Example 2

This example illustrates the preparation of (3S)-3-[4-(4'-trifluoromethyl-biphenyl-3-ylmethoxy)-phenyl]-hex-4-ynoic acid sodium salt (2.4).

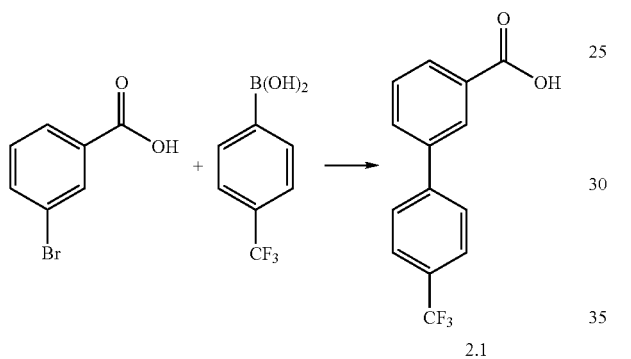

3-(4-Trifluoromethylphenyl)-benzoic acid (2.1). The Suzuki coupling was carried out according to the method of Dyer et al. (2001) *Tetrahedron Letters* 42:1765-1767. Commercially available 4-(trifluoromethyl)phenylboronic acid (15 g, 78.7 mmol) and 3-bromobenzoic acid (15.1 g, 75 mmol) were suspended in i-PrOH:water (1:4, 72 mL). 10% Pd/C (1.5 g) was added followed by aqueous $Na_2CO_3$ (39 mL, 20% by wt.). The resulting mixture was heated at 70° C. for 4 hours. The precipitate was filtered and rinsed with 20% aqueous $Na_2CO_3$ solution. The filtrate was diluted with water and acidified to pH=2. The white solid was filtered and dried in vacuo to afford 2.1 (19.69 g).

3-(4-Trifluoromethylphenyl)-benzyl alcohol (2.2). Carboxylic acid 2.1 (13.3 g, 50 mmol) in anhydrous THF (100 mL) was added dropwise to $LiAlH_4$ (2.9 g, 75 mmol) in anhydrous THF (150 mL) at 0° C. over 30 minutes. The resulting mixture was slowly warmed to room temperature and stirred for 4 hours. The reaction was slowly quenched with water (2.9 mL) at 0° C., 15% NaOH aqueous solution (2.9 mL) and another portion of water (8.7 mL). The mixture was dried over $Na_2SO_4$ and concentrated to give 2.2 as a white solid (11.9g).

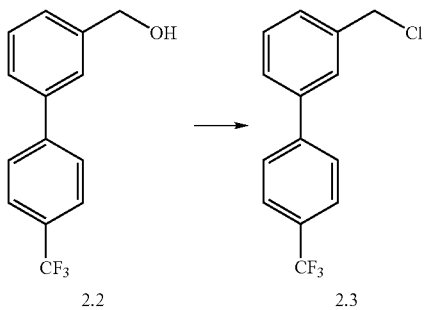

3-(4-Trifluoromethylphenyl)-benzyl chloride (2.3). The alcohol 2.2 (15 g, 59.5 mmol) was dissolved in anhydrous DCM (100 mL). Thionyl chloride (10 mL) was slowly added dropwise to the above solution. The resulting mixture was stirred at room temperature for 24 hours. The organic solvent was removed under vacuo. The residue was chromatographed ($SiO_2$ gel 60, eluted with 20% DCM in hexanes). Fractions containing the desired product 2.3 were combined and concentrated to a white solid (14.0 g). $^1H$ NMR (400 MHz) ($CDCl_3$) δ 7.73 (4H, s); 7.65 (1H, s); 7.58 (1H, s); 7.52-7.28 (2H, m); 4.69 (2H, s).

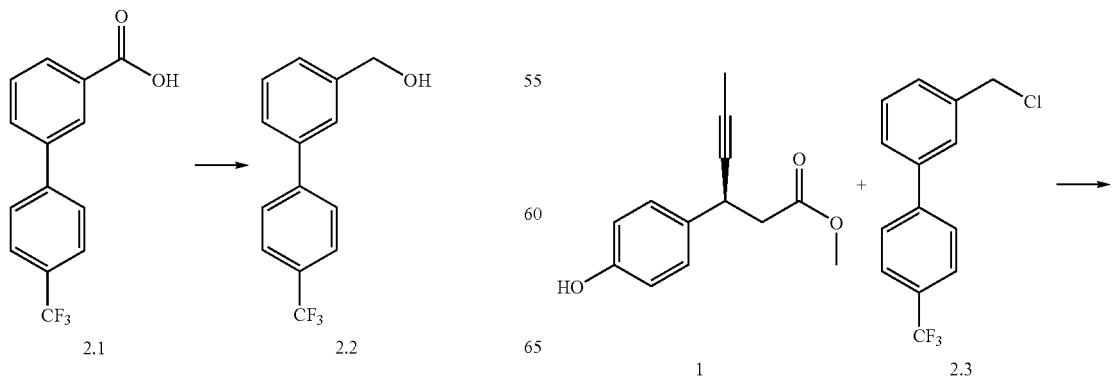

-continued

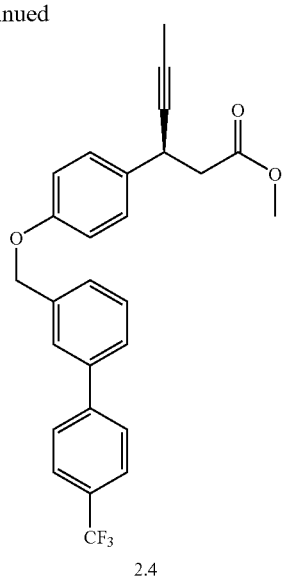
2.4

(3S)-3-[4-(4'-Trifluoromethyl-biphenyl-3-ylmethoxy)-phenyl]-hex-4-ynoic acid methyl ester (2.4). Benzyl chloride 2.3 (28.0 g, 103 mmol) and phenol 1 (21.5 g, 98 mmol) were dissolved in acetone (150 mL) and treated with $Cs_2CO_3$ (39.9 g, 122 mmol). The reaction was stirred at 50° C. for 16 hours, filtered, and concentrated to a pale yellow oil which was chromatographed (silica gel, 33% to 66% DCM in hexanes). Eluant containing compound 2.4 was concentrated to a colorless oil (40.0 g).

6.3 Example 3

This example illustrates the preparation of (S)-3-[4-(4'-chloro-2'-methyl-biphenyl-3-ylmethoxy)-phenyl]-N,N-dimethyl-succinamic acid (3).

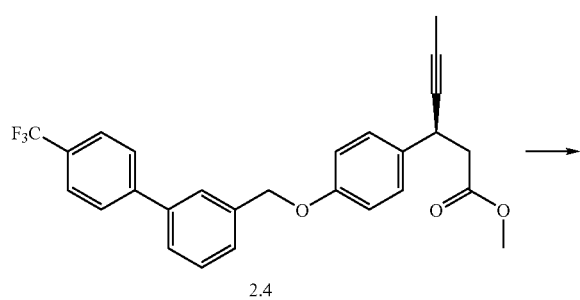
2.4

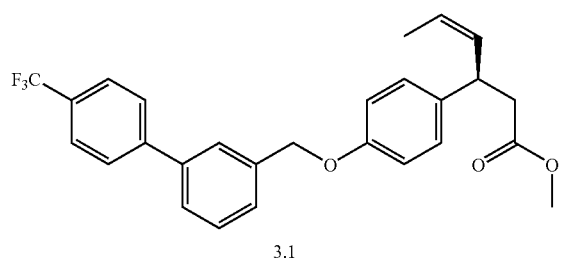
3.1

Methyl ester (3.1). Compound 2.4 (5.5 g, 12.16 mmol) was dissolved in 100 mL of EtOAc and quinoline (2 mL, 1.093 g/mL, 16.93 mmol) was added and nitrogen was bubbled through the solution for 5 minutes. 500 mg of Lindlar's catalyst was added, and a hydrogen balloon was attached. After 8 hours, the mixture was filtered through a plug of silica with EtOAc. The organic layer was washed with 2 N HCl (aq) (2×50 mL), saturated $NaHCO_3$ (aq) (1×50 mL), brine (1×50 mL) and dried with $MgSO_4$. The organic layer was filtered and concentrated under reduced pressure. The material was chromatographed on silica with 10% EtOAc/hexane to afford 3.1 (5.1 g, 11.22 mmol) as a colorless oil. MS ESI (pos.) m/e: 455.0 $(M+H)^+$.

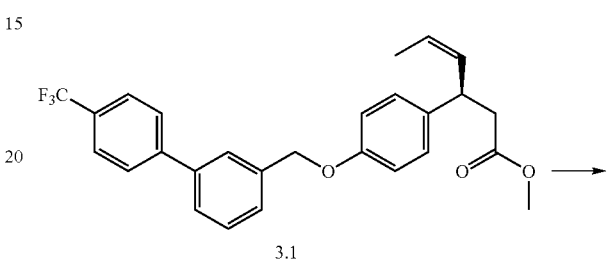
3.1

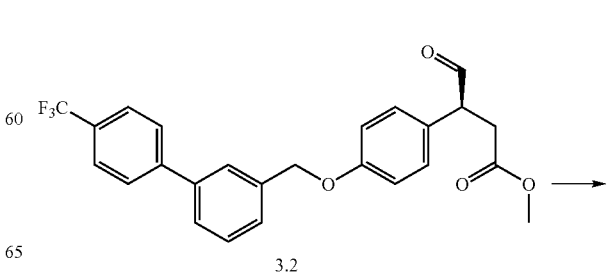
3.2

Aldehyde (3.2). Alkene 3.1 (5.1 g, 11.22 mmol) was dissolved in 100 mL of 4:1 (1,2-dioxane/water), and 2,6-lutidine (2.61 mL, 0.920 g/mL, 22.44 mmol) was added. Next, 1.2 g of a 3.4% $OsO_4$ in tBuOH (0.22 mmol) solution was added dropwise over 5 minutes. $NaIO_4$ (9.6 g, 44.88 mmol) in 25 mL of water was added. The internal reaction temperature did not rise above 30° C. After 8 hours at room temperature, the reaction mixture was diluted with 500 mL of DCM, the layers were separated, and the organic layer was washed with 0.5 M $HCl_{(aq)}$ (2×50 mL), saturated $NaHCO_3$ (aq) (1×50 mL), 5% sodium sulfite (aq) (1×50 mL), and brine. The organic layer was dried with $Na_2SO_4$, filtered, and concentrated under reduced pressure. The residue was flashed on silica with 30% EtOAc/hexanes to afford 3.2 (4.0 g, 9.09 mmol) as a yellow oil. MS ESI (pos.) m/e: 443.4 $(M+H)^+$.

-continued

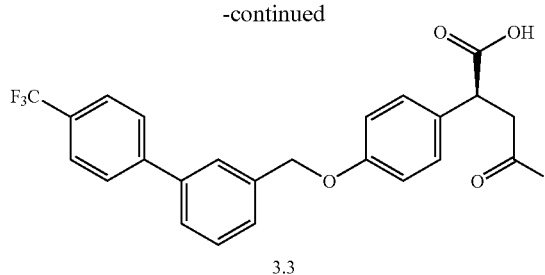

3.3

Acid (3.3). Aldehyde 3.2 (2.32 g, 5.25 mmol) was dissolved in 20 mL of acetonitrile. To this was added KH$_2$PO$_4$ (178 mg, 1.31 mmol) in 5 mL of water. The solution was cooled to −5° C. and 30% H$_2$O$_2$ (aq) (714 mg, 6.30 mmol) was added. NaClO$_2$ (712 mg, 7.88 mmol) was dissolved in 5 mL of water and added via syringe pump over 3 hours while maintaining a temperature below 0° C. After the addition of the NaClO$_2$ solution, the mixture was stirred for 1 hour. 300 mL of DCM was added, and the pH of the aqueous layer was adjusted to 2 with 2 N HCl(aq). The aqueous layer was extracted with DCM (2×100 mL), and the combined organic extracts were washed with 5% sodium sulfite (aq) (1×50 mL), and brine. The organic layer was dried with NaSO$_4$, filtered, and concentrated under reduced pressure. The residue was chromatographed on silica with 50% EtOAc/hexanes to afford 3.3 (2.12 g, 4.62 mmol) as a colorless oil. MS ESI (pos.) m/e: 459.3 (M+H)$^+$.

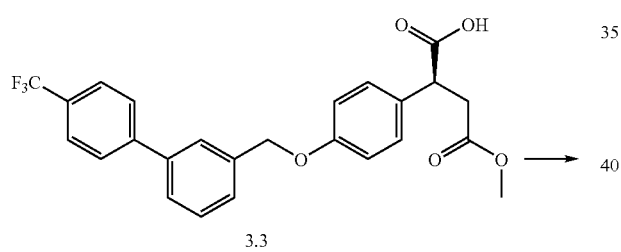

3.3

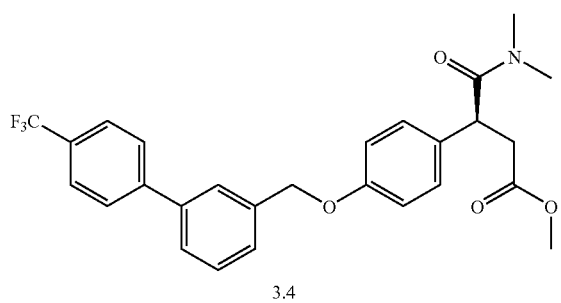

3.4

Dimethylamide (3.4). Acid 3.3 (3.5 g, 7.64 mmol) was dissolved in 50 mL of DCM. To this mixture was added 1-hydroxybenzotriazole hydrate (2.17 g, 16.04 mmol), N-(3-dimethylaminopropyl)-N'-ethylcarbondiimide hydrochloride (2.93 g, 15.28 mmol), and 2M dimethylamine in THF (7.7 mL, 15.28 mmol). The reaction was stirred for 8 hours and diluted with 400 mL of EtOAc. The organic layer was washed with 2N HCl$_{(aq)}$ (2×50 mL), NaHCO$_{3(aq)}$ (1×50 mL), brine (1×50 mL) and dried with MgSO$_4$ and filtered. The organic layer was concentrated under reduced pressure, and the residue was flashed through silica with 15% EtOAc/DCM. The combined fractions were concentrated under reduced pressure to afford 3.4 (3.4 g, 7.03 mmol) as a colorless oil.

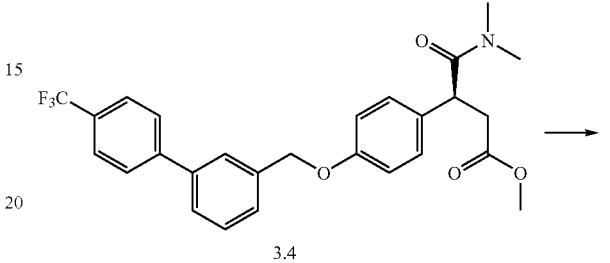

3.4

3.5

(S)-Methyl 4-(dimethylamino)-3-(4-hydroxyphenyl)-4-oxobutanoate (3.5). Dimethylamide 3.4 (2.1 g, 4.23 mmol) was dissolved in 50 mL of EtOAc, and nitrogen was bubbled through the solution for 5 minutes. 1 g of palladium on carbon (5 wt. %, wet contains 50% water) was added, and a hydrogen balloon was attached. After 8 hours, the mixture was filtered through a plug of silica with 10% MeOH in EtOAc. The organic layer was concentrated under reduced pressure and partitioned between acetonitrile (100 mL) and hexane (50 mL). The acetonitrile layer was washed with hexane (4×50 mL). The acetonitrile layer was concentrated under reduced pressure to afford (S)-methyl 4-(dimethylamino)-3-(4-hydroxyphenyl)-4-oxobutanoate 3.5 (1.0 g, 3.98 mmol) as a colorless oil. MS ESI (pos.) m/e: 252.4 (M+H)$^+$.

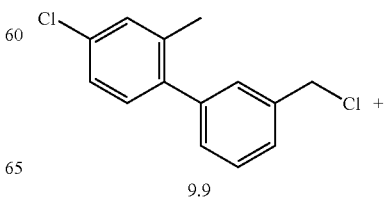

9.9

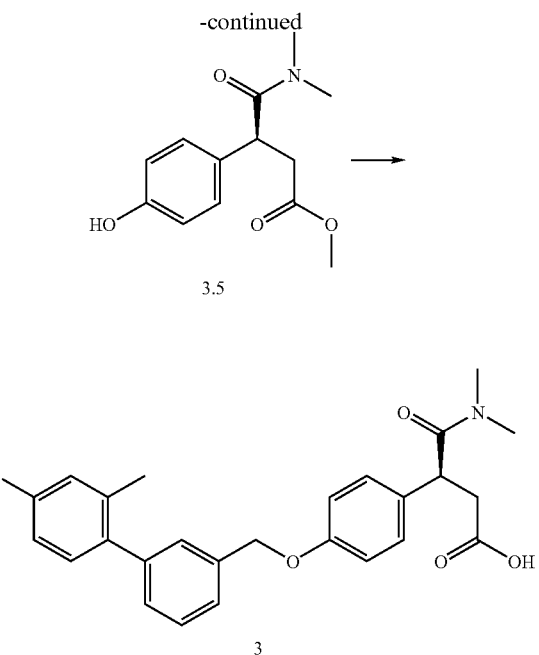

(S)-3-[4-(4'-Chloro-2'-methyl-biphenyl-3-ylmethoxy)-phenyl]-N,N-dimethyl-succinamic acid (3). The phenol 3.5 (315 mg, 1.26 mmol) was dissolved in 5 mL of DMF and benzyl chloride 9.9 (346 mg, 1.38 mmol) was added followed by cesium carbonate (600 mg, 1.88 mmol). The reaction was stirred for 14 hours and diluted with 250 mL of EtOAc. The organic layer was washed with 1N HCl (aq) (50 mL), saturated NaHCO$_3$ (aq) (50 mL), and brine (2×50 mL). The organic layer was dried with MgSO$_4$, filtered, and concentrated under reduced pressure. The residue was dissolved in 15 mL THF and 0.111 N NaOH (aq) (16 mL, 1.78 mmol) was added. MeOH (10 mL) was added and the mixture became homogeneous. The solution was stirred for 8 hours and concentrated to remove the organic solvent. The slurry was diluted with water (50 mL) and DCM (300 mL). The mixture was adjusted with 2 N HCl (aq) to a pH of 2. The material was extracted with DCM (3×75 mL). The organic layer was dried with Na$_2$SO$_4$ and concentrated under reduced pressure. The residue was flashed through silica with 3% MeOH in DCM to afford dimethylamide 3 (376 mg, 0.833 mmol) as a colorless film. $^1$H NMR (400 MHz) (CDCl$_3$) δ 7.41-7.47 (m, 2H); 7.31 (m, 1H); 7.15-7.26 (m, 6H); 6.69 (d, J=7.5 Hz, 2H); 5.10 (s, 2H); 4.24 (m, 1H); 3.16 (m, 1H); 2.99 (s, 3H); 2.94 (s, 3H); 2.70 (m, 1H), 2.24 (s, 3H).

6.4 Example 4

This example illustrates the preparation of (S)-4-(dimethylamino)-3-(4-((4-methyl-2-p-tolylthiazol-5-yl)methoxy)phenyl)-4-oxobutanoic acid (4).

(S)-4-(Dimethylamino)-3-(4-((4-methyl-2-p-tolylthiazol-5-yl)methoxy)phenyl)-4-oxobutanoic acid (4). Thiazyl chloride 4.8 was prepared according to the method described in Example 2 starting from commercially available 4-methyl-2-(4-methylphenyl)-1,3-thiazole-5-carboxylic acid. The phenol 3.5 (276 mg, 1.10 mmol) was dissolved in 5 mL of DMF and thiazyl chloride 4.8 (317 mg, 1.16 mmol) was added followed by cesium carbonate (715 mg, 2.20 mmol). The reaction was stirred for 14 hours and diluted with 250 mL of EtOAc. The organic layer was washed with 1N HCl (aq) (50 mL), saturated NaHCO$_3$ (aq) (50 mL), and brine (2×50 mL). The organic layer was dried with MgSO$_4$, filtered, and concentrated under reduced pressure. The residue was dissolved in 15 mL THF and 0.111 N NaOH (aq) (15 mL, 1.65 mmol) was added. MeOH (10 mL) was added and the mixture became homogeneous. The solution was stirred for 8 hours and concentrated to remove the organic solvent. The slurry was diluted with water (50 mL) and DCM (300 mL). The mixture was adjusted with 2N HCl (aq) to a pH of 2. The material was extracted with DCM (3×75 mL). The organic layer was dried with Na$_2$SO$_4$ and concentrated under reduced pressure. The residue was flashed through silica with 5% MeOH in DCM to afford dimethylamide 4 (346 mg, 0.79 mmol) as a white solid. $^1$H NMR (400 MHz) (CDCl$_3$) δ 7.83 (d, J=8.0, 2H); 7.20-7.28 (m, 4H); 6.96 (d, J=8.5, 2H); 5.17 (s, 2H); 4.22 (dd, J=3.8, 8.9 Hz, 1H); 3.13 (dd, J=8.9, 15.8 Hz, 1H); 3.02 (s, 3H); 2.93 (s, 3H); 2.80 (dd, J=3.8, 15.8 Hz, 1H); 2.51 (s, 3H); 2.41 (s, 3H).

6.5 Example 5

This example illustrates the preparation of (S)-3-(2-methyl-2H-1,2,4-triazol-3-yl)-3-[4-(4'-trifluoromethyl-biphenyl-3-ylmethoxy)-phenyl]-propionic acid (5).

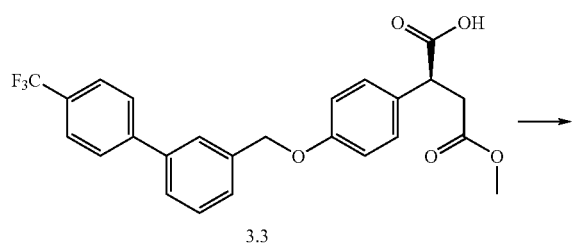

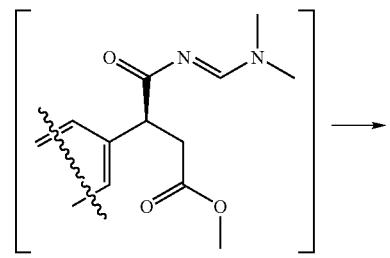

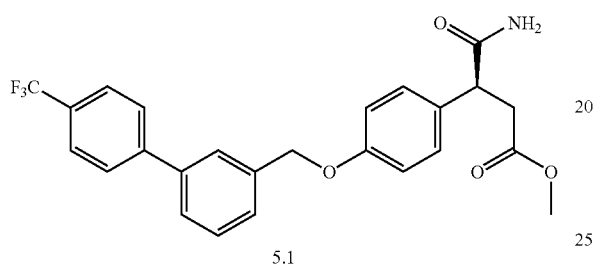

Amide (5.1). Acid 3.3 (6.0 g, 13.1 mmol) was dissolved in 100 mL of DCM. To this was added 1-hydroxybenzotriazole hydrate (3.7 g, 27.5 mmol), N-(3-dimethylaminopropyl)-N'-ethylcarbondiimide hydrochloride (5.0 g, 26.2 mmol), and 2M ammonia in n-PrOH (14 mL, 26.2 mmol). The reaction was stirred for 8 hours and diluted with 500 mL of EtOAc. The organic layer was washed with 2N HCl (aq) (2×75 mL), NaHCO$_3$ (aq) (1×75 mL), and brine (1×75 mL) and dried with MgSO$_4$ and filtered. The organic layer was concentrated under reduced pressure, and the residue was flashed through silica with 25% EtOAc/DCM. The combined fractions were concentrated under reduced pressure to afford 5.1 (5.3 g, 11.5 mmol) as a colorless oil.

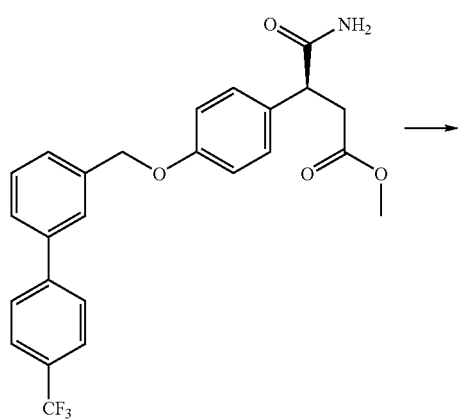

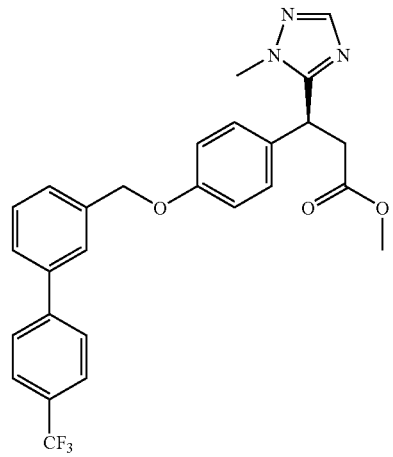

(S)-3-(2-Methyl-2H-1,2,4-triazol-3-yl)-3-[4-(4'-trifluoromethyl-biphenyl-3-ylmethoxy)-phenyl]-propionic acid (5). Amide 5.1 (6.48 g, 14.2 mmol) was dissolved in 7 mL of N,N-dimethylformamide dimethyl acetal (119.17 MW, 0.894 g/mL, 52.6 mmol). The solution was gradually heated to 80° C. over 30 minutes. The mixture was allowed to cool to 35° C., and the sample was concentrated under reduced pressure. The residue was dissolved in 20 mL of acetic acid followed by careful addition of methylhydrazine (5 mL, 0.866 g/mL, 94.0 mmol) over 5 minutes (the acid/base exotherm was used to run the reaction). The temperature increased to 65° C., and an oil bath at 80° C. was used to finish the reaction. The total heating time was 45 minutes. The reaction was allowed to come to room temperature, and was diluted with 500 mL of DCM. The organic layer was washed with water (3×100 mL), brine (1×100 mL), dried with Na$_2$SO$_4$, filtered, and concentrated to a residue. The material was flashed on silica with 10% acetonitrile/DCM to afford methyltriazole 5 (4.3 g, 8.7 mmol) as a yellow oil. MS ESI (pos.) m/e: 496.5 (M+H)$^+$.

6.6 Example 6

This example illustrates the preparation of (S)-3-[4-(4'-chloro-2'-methyl-biphenyl-3-ylmethoxy)-phenyl]-3-(2-methyl-2H-1,2,4-triazol-3-yl)-propionic acid (6).

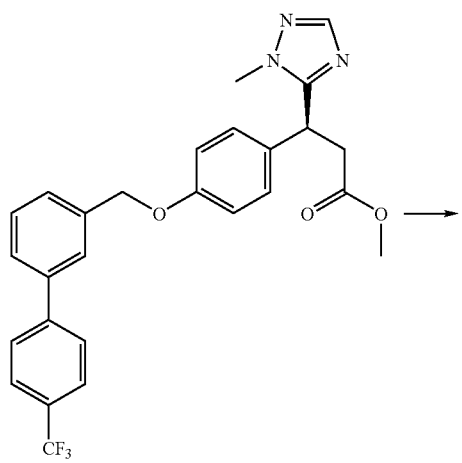

5

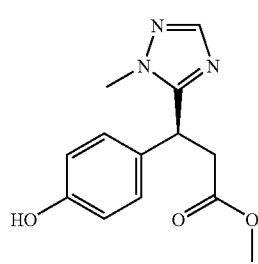

6.1

(S)-Methyl 3-(4-hydroxyphenyl)-3-(2-methyl-2H-1,2,4-triazol-3-yl)propanoate (6.1). Methyltriazole 5 (2.78 g, 5.61 mmol) was dissolved in 50 mL of EtOAc, and nitrogen was bubbled through the solution for 5 minutes. 1 g of palladium on carbon (5 wt. %, wet contains 50% water) was added, and a hydrogen balloon was attached. After 8 hours, the mixture was filtered through a plug of silica with 10% MeOH in EtOAc. The organic layer was concentrated under reduced pressure and partitioned between acetonitrile (100 mL) and hexane (50 mL). The acetonitrile layer was washed with hexane (4×50 mL). The acetonitrile layer was concentrated under reduced pressure to afford (S)-methyl 3-(4-hydroxyphenyl)-3-(2-methyl-2H-1,2,4-triazol-3-yl)propanoate 6.1 (1.30 g, 4.99 mmol) as a colorless oil. MS ESI (pos.) m/e: 262.4 (M+H)⁺.

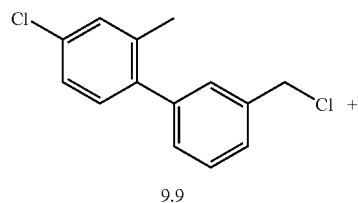

9.9

-continued

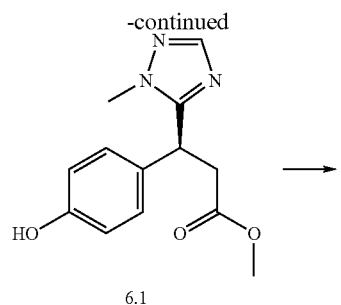

6.1

(S)-3-[4-(4'-Chloro-2'-methyl-biphenyl-3-ylmethoxy)-phenyl]-3-(2-methyl-2H-1,2,4-triazol-3-yl)-propionic acid (6). The phenol 6.1 (21 mg, 0.081 mmol) was dissolved in 1 mL of DMF and benzyl chloride 9.9 (22 mg, 0.089 mmol) was added followed by cesium carbonate (52 mg, 0.161 mmol). The reaction was stirred for 14 hours and diluted with 50 mL of EtOAc. The organic layer was washed with 1N HCl (aq) (10 mL), saturated NaHCO₃ (aq) (10 mL), and brine (2×10 mL). The organic layer was dried with MgSO₄, filtered, and concentrated under reduced pressure. The residue was dissolved in 2 mL THF and 0.111 N NaOH (aq) (1.1 mL, 0.12 mmol) was added. MeOH (1 mL) was added and the mixture became homogeneous. The solution was stirred for 8 hours and concentrated to remove the organic solvent. The slurry was dissolved in DMSO and the pH was brought to a pH of 2 with 2N HCl (aq). The material was chromatographed using HPLC. The combined fractions were combined and concentrated to afford methyltriazole 6 (22 mg, 0.049 mmol) as a colorless film. $^1$H NMR (400 MHz) (CDCl₃) δ 8.68 (bs, 1H); 8.11 (s, 1H); 7.32-7.45 (m, 2H); 7.33 (s, 1H); 7.21-7.28 (m, 5H); 7.16 (d, J=8.4 Hz, 2H); 6.97 (d, J=8.7 Hz, 2H); 5.09 (s, 2H); 4.63 (dd, J=4.9, 10.2 Hz, 1H); 3.83 (s, 3H); 3.54 (dd, J=10.2, 17.4 Hz, 1H); 3.06 (dd, J=4.9, 17.4 Hz, 1H); 2.23 (s, 3H).

6.7 Example 7

This example illustrates the preparation of (S)-3-(1-methyl-1H-tetrazol-5-yl)-3-[4-(4'-trifluoromethyl-biphenyl-3-ylmethoxy)-phenyl]-propionic acid (7).

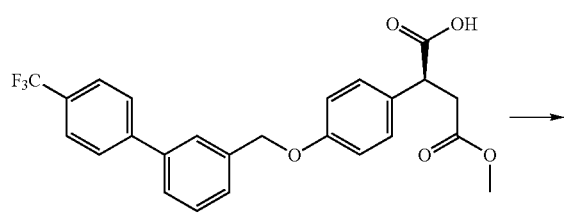

3.3

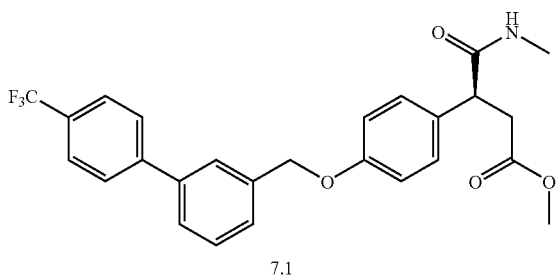

7.1

Methylamide (7.1). Acid 3.3 (6.0 g, 13.1 mmol) was dissolved in 100 mL of DCM. To this mixture was added 1-hydroxybenzotriazole hydrate (3.7 g, 27.5 mmol), N-(3-dimethylaminopropyl)-N'-ethylcarbondiimide hydrochloride (5.0 g, 26.2 mmol), and 2M methylamine in THF (14 mL, 26.2 mmol). The reaction was stirred for 8 hours, diluted with 500 mL of EtOAc, and the organic layer was washed with 2N HCl(aq) (2×75 mL), NaHCO₃ (aq) (1×75 mL), brine (1×75 mL) and dried with MgSO₄ and filtered. The organic layer was concentrated under reduced pressure, and the residue was flashed through silica with 15% EtOAc/DCM. The combined fractions were concentrated under reduced pressure to afford 7.1 (4.2 g, 11.5 mmol) as a colorless oil. MS ESI (pos.) m/e: 472.3 (M+H)⁺.

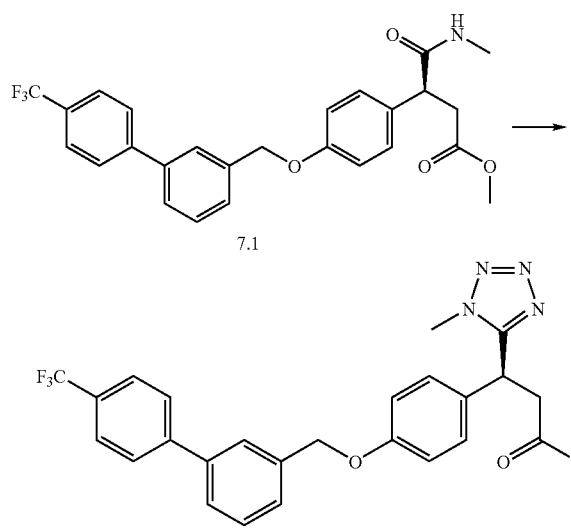

(S)-3-(1-Methyl-1H-tetrazol-5-yl)-3-[4-(4'-trifluoromethyl-biphenyl-3-ylmethoxy)-phenyl]-propionic acid (7). Methylamide 7.1 (2.15 g, 4.59 mmol) was dissolved in 50 mL of acetonitrile. NaN₃ (900 mg, 13.8 mmol) was added followed by the dropwise addition of Tf₂O (5.2 g, 18.4 mmol). The temperature rose to 34° C. The reaction was stirred for 12 hours and diluted with 250 mL of DCM. The organic layer was washed with NaHCO₃ (aq) (2×50 mL), brine (1×50 mL) and dried with MgSO₄ and filtered. The organic layer was concentrated under reduced pressure, and the residue was flashed through silica with 15% EtOAc/DCM. The combined fractions were concentrated under reduced pressure to afford methyltetrazole 7 (1.52 g, 3.07 mmol) as a colorless oil. MS ESI (pos.) m/e: 497.4 (M+H)⁺.

6.8 Example 8

This example illustrates the preparation of (S)-3-[4-(4'-chloro-2'-methyl-biphenyl-3-ylmethoxy)-phenyl]-3-(1-methyl-1H-tetrazol-5-yl)-propionic acid (8).

(S)-Methyl 3-(4-hydroxyphenyl)-3-(1-methyl-1H-tetrazol-5-yl)propanoate (8.1). Methyltetrazole 7 (413 mg, 0.833 mmol) was dissolved in 5 mL of EtOAc and nitrogen was bubbled through the solution for 5 minutes. Palladium on carbon (200 mg, 5 wt. %, wet contains 50% water) was added, and a hydrogen balloon was attached. After 8 hours, the mixture was filtered through a plug of silica with 10% MeOH in EtOAc. The organic layer was concentrated under reduced pressure and partitioned between acetonitrile (10 mL) and hexane (5 mL). The acetonitrile layer was washed with hexane (4×5 mL). The acetonitrile layer was concentrated under reduced pressure to afford (s)-methyl 3-(4-hydroxyphenyl)-3-(1-methyl-1H-tetrazol-5-yl)propanoate (8.1) (203 mg, 0.775 mmol) as a colorless oil.

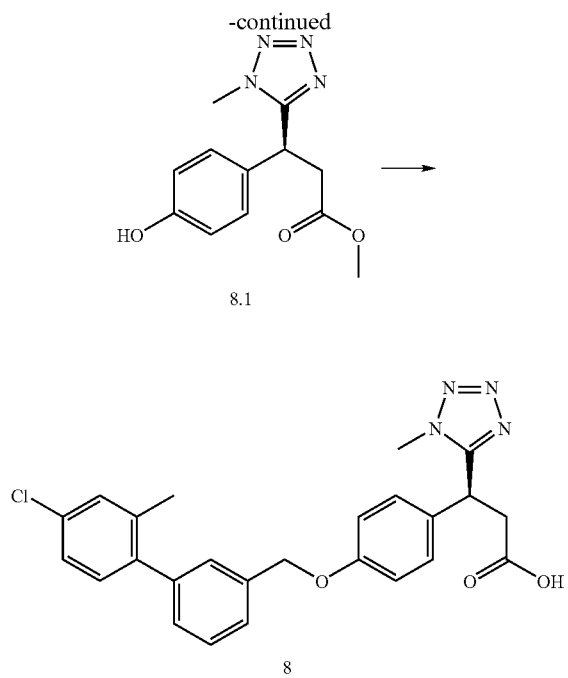

(S)-3-[4-(4'-Chloro-2'-methyl-biphenyl-3-ylmethoxy)-phenyl]-3-(1-methyl-1H-tetrazol-5-yl)-propionic acid (8). The phenol 8.1 (42 mg, 0.160 mmol) was dissolved in 1 mL of DMF and benzyl chloride 9.9 (45 mg, 0.1763 mmol) was added followed by cesium carbonate (78 mg, 0.241 mmol). The reaction was stirred for 14 hours and diluted with 50 mL of EtOAc. The organic layer was washed with 1N HCl (aq) (10 mL), saturated NaHCO₃ (aq) (10 mL), and brine (2×10 mL). The organic layer was dried with MgSO₄, filtered and concentrated under reduced pressure. The residue was dissolved in 2 mL THF and 0.111 N NaQH (aq) (1.1 mL, 0.12 mmol) was added. MeOH (1 mL) was added, and the mixture became homogeneous. The solution was stirred for 8 hours and concentrated to remove the organic solvent. The slurry was dissolved in DMSO and the pH was brought to a pH of 2 with 2N HCl (aq). The material was chromatographed using HPLC. The combined fractions were concentrated to afford methyltetrazole 8 (59 mg, 0.128 mmol) as a colorless film. ¹H NMR (400 MHz, CDCl₃) δ 7.38-7.43 (m, 2H); 7.31 (s, 1H); 7.19-7.26 (m, 4H); 7.13 (dd, J=1.9, 8.3 Hz, 2H); 6.93 (d, J=8.7 Hz, 2H); 5.07 (s, 2H); 4.55 (dd, J=5.6, 9.4 Hz 1H); 3.81 (s, 3H); 3.58 (dd, J=9.4, 17.4 Hz, 1H); 3.05 (dd, J=5.6, 17.4 Hz, 1H); 2.20 (s, 3H).

6.9 Example 9

This example illustrates the preparation of (S)-3-[4-(4'-chloro-2'-methyl-biphenyl-3-ylmethoxy)-phenyl]-3-(1-methyl-1H-imidazol-2-yl)-propionic acid (9).

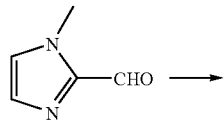

(1-Methyl-1H-imidazol-2-yl)(4-(tetrahydro-2H-pyran-2-yloxy)phenyl)methanol (9.1). 4-(2-Tetrahydro-2H-pyranoxy)phenylmagnesium bromide (0.5M in THF, 160 mL, 80 mmol) was added slowly to a solution of 1-methyl-2-imidazolecarboxaldehyde (8 g, 72.7 mmol) in THF (100 mL) via syringe at −78° C. The reaction mixture was stirred at this temperature for 3 hours and quenched with saturated NH₄Cl (aq). The mixture was extracted with EtOAc (2×100 mL), and the combined organic extracts were dried over Na₂SO₄, filtered, and concentrated under reduced pressure to afford 9.1 as a colorless oil (21 g), which was used directly in the next step.

(1-Methyl-1H-imidazol-2-yl)(4-(tetrahydro-2H-pyran-2-yloxy)phenyl)methanone (9.2). Pyridinium dichromate (36 g, 95.7 mmol) was added to a solution of 9.1 (21 g, 72.7 mmol) in DCM (100 mL) at 0° C. in several portions. The mixture was stirred at 0° C. for 1 hour and at room temperature for 6 hours. Silica gel (75 g) was added to the reaction mixture, and the resulting slurry was filtered through a pad of silica gel. The solid was washed with DCM (200 mL). The filtrate was washed with water and saturated brine, dried over Na₂SO₄, filtered and concentrated under reduced pressure to give an oily residue, which was flash chromatographed (silica gel, 0-30% EtOAc in hexane) to afford ketone 9.2 as yellow solid (16 g). ¹H NMR (500 MHz) (CDCl₃) δ 8.33-8.35 (m, 2H); 7.10-7.29 (m, 4H); 5.56 (t, J=3.0 Hz, 1H); 4.08 (s, 3H); 3.85-3.90 (m, 1H); 3.61-3.65 (m, 1H); 2.03 (m, 1H); 1.90-1.91 (m, 2H); 1.69-1.74 (m, 2H); 1.61-1.64 (m, 1H).

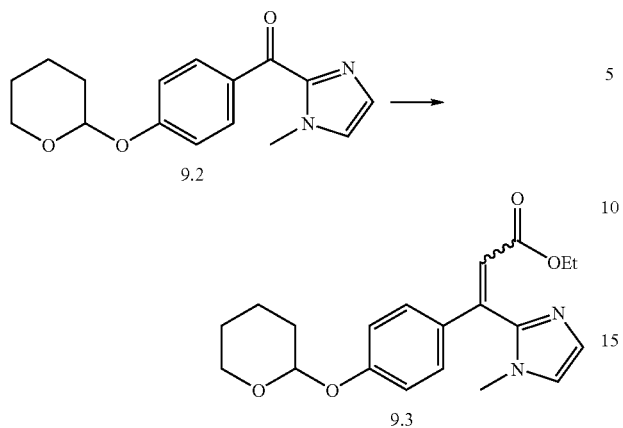

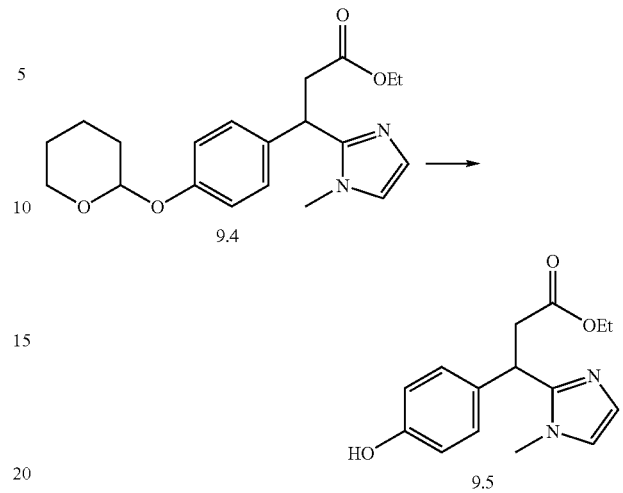

(Z/E)-Ethyl 3-(1-methyl-1H-imidazol-2-yl)-3-(4-(tetrahydro-2H-pyran-2-yloxy)phenyl)acrylate (9.3). A solution of lithium hexamethyldisilazide (1M in THF, 64 mL) was added slowly to a stirred solution of ethyl (trimethylsilyl) acetate (9.9 g, 61.5 mmol) and ketone 9.2 (16 g, 55.9 mmol) in anhydrous THF (60 mL) via syringe at −78° C. The reaction mixture was stirred at this temperature for 2 hours. The reaction temperature was allowed to rise to −20° C. over 6 hours. The reaction mixture was quenched with saturated ammonium chloride (aq) at this temperature, extracted with EtOAc (2×150 mL), and dried over Na$_2$SO$_4$. After filtration, the solvent was removed under reduced pressure to afford 9.3 as a colorless oil (21 g, including some ethyl (trimethylsilyl) acetate), which was used directly in the next step. LC-MS ESI (pos.) m/e: 357 (M+H).

(+/−)-Ethyl 3-(4-hydroxyphenyl)-3-(1-methyl-1H-imidazol-2-yl)propanoate (9.5). Trifluoroacetic acid (21 mL) was added to a solution of protected ester 9.4 (21 g) in dry DCM (210 mL) with caution at 0° C. The mixture was brought to room temperature over 4 hours. The reaction mixture was concentrated under reduced pressure to provide a yellow oily residue, which was re-dissolved in DCM (200 mL) and washed with water, saturated NaHCO$_3$, water and brine, and dried over Na$_2$SO$_4$. After filtration, the solvent was removed under reduced pressure, and the product was crystallized in EtOAc-hexane. The mother liquid was concentrated and flash chromatographed (silica gel, 50% EtOAc in hexane as eluant). The product, (±)-ethyl 3-(4-hydroxyphenyl)-3-(1-methyl-1H-imidazol-2-yl)propanoate (9.5) was obtained as a colorless crystal (combined yield 11 g). LC-MS ESI (pos.) m/e: 275 (M+H). $^1$H NMR (500 MHz) (CDCl$_3$) δ 9.28 (s, 1H); 6.98-7.00 (m, 3H); 6.65-6.77(m, 3H); 4.41 (dd, J=9.0, 3.0 Hz, 1H); 3.96 (q, J=7.0, 2H); 3.39 (s, 3H); 3.19 (dd, J=16.0, 7.0 Hz, 1H); 2.78 (dd, J=16.0, 6.5 Hz, 1H); 1.80 (t, J=7.0 Hz, 3H).

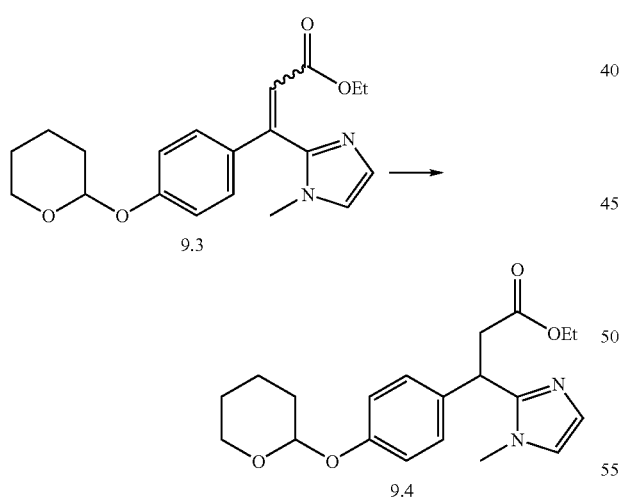

(+/−)-Ethyl 3-(1-methyl-1H-imidazol-2-yl)-3-(4-(tetrahydro-2H-pyran-2-yloxy)phenyl)propanoate (9.4). A solution of olefin 9.3 (21 g, 55.9 mmol) in EtOH (200 mL) was stirred with 10% Pd—C (2.1 g, 2 mmol) under a hydrogen atmosphere (provided by a balloon) at room temperature overnight. The reaction mixture was filtered through a silica gel pad and concentrated to provide protected ester 9.4 as an off-white oil (21 g), which was used directly in the next step. LC-MS ESI (pos.) m/e: 359 (M+H).

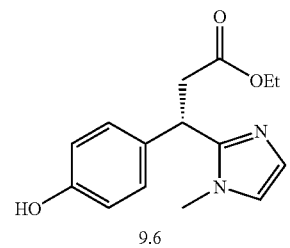

(S)-Ethyl 3-(4-hydroxyphenyl)-3-(1-methyl-1H-imidazol-2-yl)propanoate (9.6). Racemic compound 9.5 was separated on a preparatory chiral HPLC with CHIRALPAK AD column, using 11% i-PrOH in hexane as eluant. Eluant containing the peak with greater retention time was concentrated and compound 9.6 was obtained as colorless crystals. The absolute configuration was assigned by analogy to other GPR40 agonist compounds.

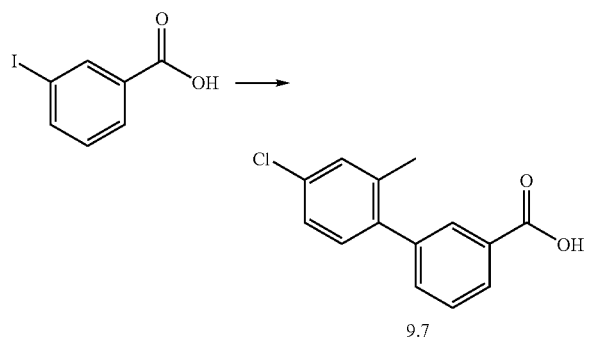

4'-Chloro-2'-methyl-biphenyl-3-carboxylic acid (9.7). To a mixture of 3-iodobenzoic acid (11.9 g, 48 mmol), 4-chloro-2-methylphenylboronic acid (9.8 g, 57.7 mmol) and sodium carbonate (6.1 g, 57.7 mmol) under nitrogen atmosphere, was added i-PrOH-water (1/1, 180 mL) followed by 10% Pd—C (2 g, 19.2 mmol) with caution. The reaction mixture was heated at 80° C. under nitrogen overnight. The catalyst was removed by filtration, and the filtered catalyst was washed with EtOH (60 mL). Most of organic solvent was removed under reduced pressure. The resulting aqueous residue was treated with 2N HCl (aq) to bring the pH <2. The resulting mixture was extracted with EtOAc (2×100 mL). The combined organic extracts were washed with water and saturated brine, dried over $Na_2SO_4$, filtered and concentrated under reduced pressure. Compound 9.7 was obtained as white solid (12 g), which was used directly in the next step. MS ESI (neg.) m/e: 245 (M−H).

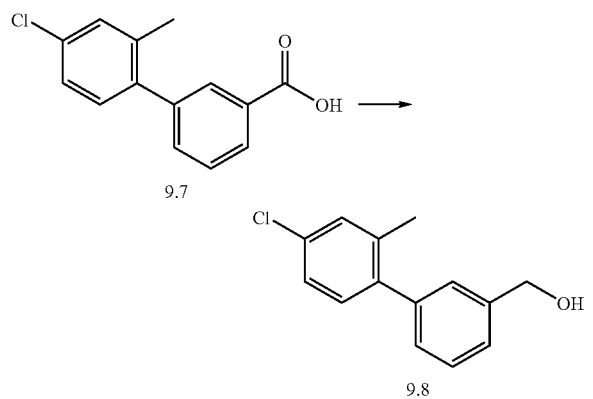

4'-Chloro-2'-methyl-biphenyl-3-yl)-methanol (9.8). $LiAlH_4$ (1.0 M in THF, 50 mL, 50 mmol) was added slowly to solution of 9.7 (6.0 g, 24.4 mmol) in THF (40 mL) via syringe at 0° C., under nitrogen atmosphere. The reaction mixture was brought to room temperature by stirring overnight. The reaction mixture was quenched with cold water with caution. The reaction mixture was filtered through a short pad of silica gel after treating with Celite® (6 g). The filtered solid cake was washed with EtOAc (150 mL). The combined organic extracts were concentrated under reduced pressure and re-dissolved in EtOAc (150 mL). The resulting organic solution was washed with NaOH (10% in water, 30 mL), water and saturated brine, dried over $Na_2SO_4$, filtered and concentrated under reduced pressure. Compound 9.8 was obtained as colorless oil (5.4 g) which was used directly in the next step. LC-MS ESI (pos.) m/e: 233 (M+H), 215(M+H—$H_2O$).

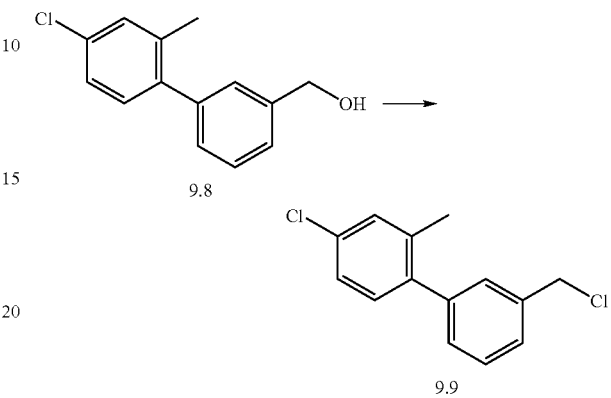

4-Chloro-3'-chloromethyl-2-methyl-biphenyl (9.9). $SOCl_2$ (12 mL) was added slowly to a solution of 9.8 (5.4 g, 23.2 mmol) in DCM (100 mL) via syringe at 0° C., under nitrogen atmosphere. The reaction mixture was brought to room temperature by stirring overnight. The solvent was removed under reduced pressure, and the residue was flash chromatographed (silica gel, 0-5% EtOAc in hexane). Compound 9.9 was obtained as colorless oil (5.2 g). LC-MS ESI (pos.) m/e: 251 (M+H), 215(M+H—HCl). $^1$H NMR (500 MHz) ($CDCl_3$) δ 7.17-7.44 (m, 7H); 4.65 (s, 2H); 2.27 (s, 3H).

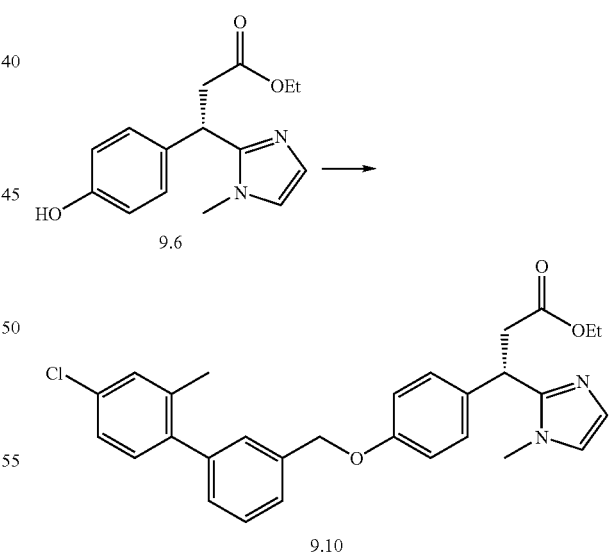

(S)-3-[4-(4'-Chloro-2'-methyl-biphenyl-3-ylmethoxy)-phenyl]-3-(1-methyl-1H-imidazol-2-yl)-propionic acid ethyl ester (9.10). $Cs_2CO_3$ (72 mg, 0.22 mmol) and compound 9.9 (53 mg, 0.21 mmol) were added successively to a solution of (S)-ethyl 3-(4-hydroxyphenyl)-3-(1-methyl-1H-imidazol-2-yl)propanoate (9.6) (55 mg, 0.2 mmol) in dry DMF (3 mL). The reaction mixture was stirred at room temperature overnight, diluted with EtOAc (60 mL), washed with water and brine, dried over Na₂SO₄, filtered and concentrated under vacuum. The residue was flash chromatographed on silica gel (0-5% MeOH in DCM) to afford (S)-ethyl 3-(4-[3-(4-chloro-2-methylphenyl)benzyloxy]phenyl)-3-(1-methyl-1H-imidazol-2-yl)propanoate (9.10) as a colorless oil (97 mg). LC-MS ESI (pos.) m/e: 489 (M+H).

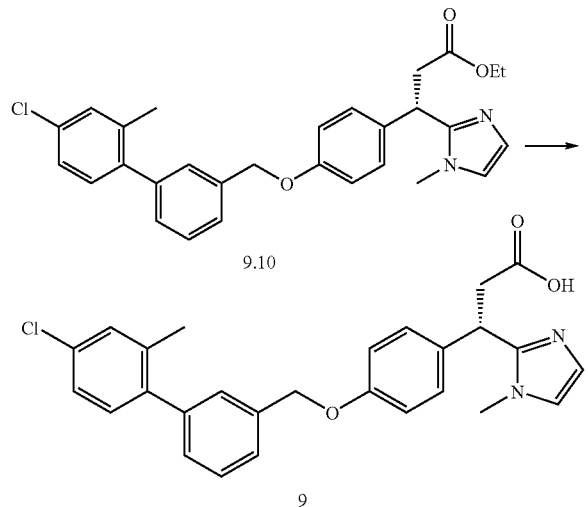

(S)-3-[4-(4'-Chloro-2'-methyl-biphenyl-3-ylmethoxy)-phenyl]-3-(1-methyl-1H-imidazol-2-yl)-propionic acid (9). 10% NaOH (aq) (1 mL) was added to a solution of (S)-ethyl 3-(4-[3-(4-chloro-2-methylphenyl)benzyloxy]phenyl)-3-(1-methyl-1H-imidazol-2-yl)propanoate (9.10) (49 mg, 0.1 mmol) in EtOH (2 mL). The reaction mixture was stirred at room temperature for 4 hours. 1N HCl was added to neutralize the mixture to pH 6-7. The mixture was extracted with EtOAc (2×20 mL), washed with water and brine, dried over Na₂SO₄, filtered and concentrated under reduced pressure. The residue was flash chromatographed (silica gel, 0-10% MeOH in DCM) to afford (S)-3-[4-(4'-chloro-2'-methyl-biphenyl-3-ylmethoxy)-phenyl]-3-(1-methyl-1H-imidazol-2-yl)-propionic acid (9) as a colorless oil. MS ESI (neg.) m/e: 459 (M–H). ¹H NMR (500 MHz) (DMSO) δ 7.87 (broad s, 1H); 6.63-7.46 (m, 13H); 5.06 (s, 2H); 4.49 (dd, J=8.4, 3.2 Hz, 1H); 3.39 (s, 3H); 3.29 (dd, J=15.0, 8.5 Hz, 1H); 3.10 (dd, J=15.2, 3.0 Hz, 1H); 2.23 (s, 3H).

6.10 Example 10

This example illustrates the preparation of (S)-3-[4-(5'-methyl-2'-butoxybiphenylmethoxy)phenyl]-3-(oxazol-2-yl)propanoic acid (10).

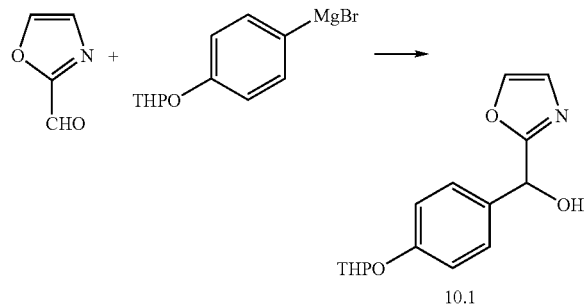

Oxazol-2-yl(4-(tetrahydro-2H-pyran-2-yloxy)phenyl)methanol (10.1). 4-(2-Tetrahydro-3H-pyranoxy)phenylmagnesium bromide (0.5 M in THF, 6.7 mmol) was added dropwise to a solution of oxazole-2-carbaldehyde (5.15 mmol) in THF (8 mL). After stirring at room temperature for 2.5 hours, the reaction was quenched with water, extracted with EtOAc (200 mL), the organic phase was washed with brine, dried over anhydrous sodium sulfate, filtered, and concentrated under reduced pressure. The residue was chromatographed (silica gel, 1:2 EtOAc/hexane) to obtain compound 10.1 (3.1 mmol). MS ESI (pos.) m/e:276(M+H). ¹H NMR (400 MHz) (DMSO-d₆) δ 8.02 (s, 1H); 7.31 (d, J=8.7 Hz, 2H); 7.14 (s, 1H); 6.97-7.01 (m, 2H); 6.27 (d, J=5 Hz, 1H); 5.74 (d, J=5 Hz, 1H); 5.44 (s, 1H); 3.74 (m, 1H); 3.52 (M, 1h); 1.72-1.81 (m, 3H); 1.52-1.60(m, 4H).

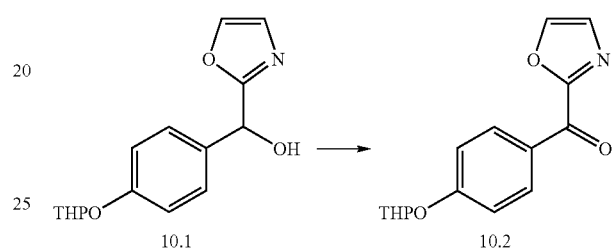

Oxazol-2-yl(4-(tetrahydro-2H-pyran-2-yloxy)phenyl)methanone (10.2). PCC (14.5 mmol, 20% w/w on silica gel) was added to a solution of 10.1 (2.91 mmol) in DCM (20 mL). After 1 hour, the reaction mixture was chromatographed (silica gel, 1:2 EtOAc/hexane) to obtain compound 10.2 (2.41 mmol). MS ESI (pos.) m/e:296.0 (M+Na). ¹H NMR (500 MHz) (DMSO-d₆) δ 8.52 (s, 1H); 8.43 (d, J=9 Hz, 2H); 7.67 (s, 1H); 7.23 (d, J=9 Hz, 2H); 5.71 (m, 1H); 3.74-3.76 (m, 1H); 3.62-3.65 (m, 1H); 1.88-1.91 (m, 2H); 1.81-1.82 (m, 1H); 1.59-1.67 (m, 3H).

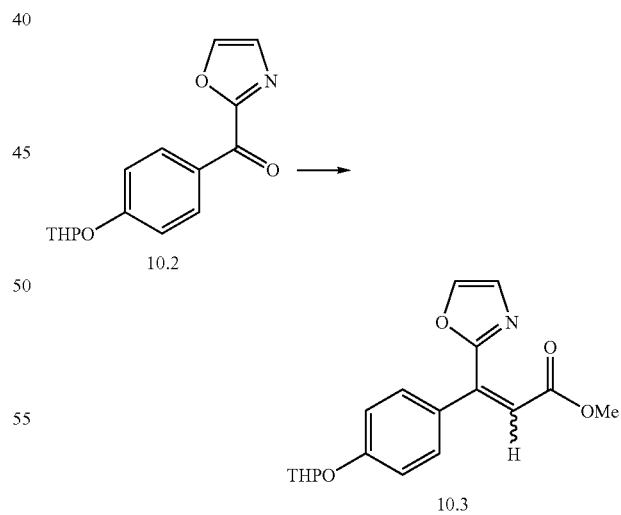

Methyl 3-(oxazol-2-yl)-3-(4-(tetrahydro-2H-pyran-2-yloxy)phenyl)acrylate (10.3). Lithium bis(trimethylsilyl)amide (3.46 mmol, 1M in THF) was added dropwise to a solution of methyl trimethylsilylacetate (3.46 mmol) in THF (5 mL) at −78° C. After 20 minutes at −78° C., a solution of 10.2 (2.16 mmol) in THF (9 mL) was added dropwise and the reaction was maintained at −78° C. for 1.5 hours. The reaction was quenched with water and extracted with EtOAc. The organic phase was washed with brine, dried over anhydrous sodium sulfate, filtered, and concentrated under reduced pressure. The residue was chromatographed (silica gel, 1:1 EtOAc/hexane) to afford compound 10.3. MS ESI (pos.) m/e 330.1 (M+1).

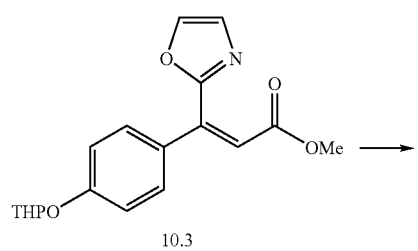

10.3

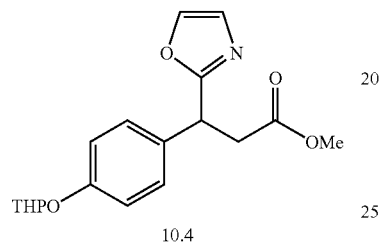

10.4

Methyl 3-(oxazol-2-yl)-3-(4-(tetrahydro-2H-pyran-2-yloxy) phenyl)propanoate (10.4). A mixture of compound 10.3 (2.55mmol) and Pd—C (440 mg) in MeOH was stirred under hydrogen at room temperature for 30 minutes. The Pd—C was removed by filtration through silica gel with EtOAc as eluant. After concentration, the residue was chromatographed (silica gel, 1:1 EtOAc/hexane) to afford compound 10.4. MS ESI (pos.) m/e 332.2 (M+1).

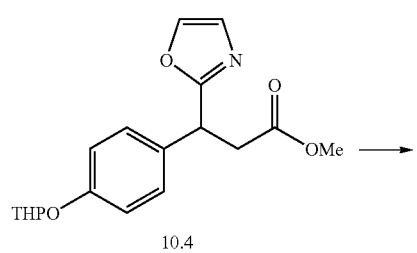

10.4

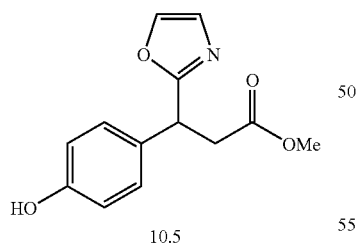

10.5

Methyl 3-(4-hydroxyphenyl)-3-(oxazol-2-yl)propanoate (10.5). A mixture of compound 10.4 (2.1 mmol), p-toluenesulfonic acid monohydrate (0.57 mmol) in MeOH (15 mL) was stirred at room temperature for 1.5 hours. After quenching with saturated aqueous NaHCO₃, MeOH was removed under reduced pressure. The residue was extracted with EtOAc, and the combined organic extracts were washed with saturated brine, dried over anhydrous sodium sulfate, and filtered through short plug of silica gel. Upon concentration, compound 10.3 was obtained. MS ESI (pos.) m/e 248.1 (M+1). $^1$H NMR (500 MHz) (DMSO-d$_6$) δ 9.04 (s, 1H); 7.99 (s, 1H); 7.14 (s, 1H); 7.05(m, 2H); 6.72 (m, 2H); 4.49-4.52 (m, 1H); 3.57 (s, 1H); 3.22-3.27(m, 1H); 2.89-2.94(m, 1H).

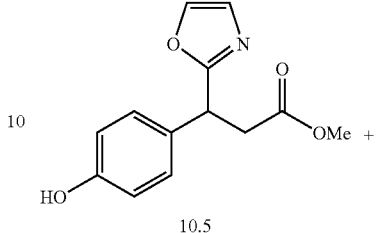

10.5

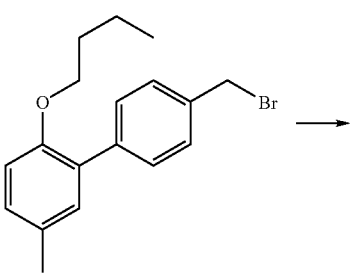

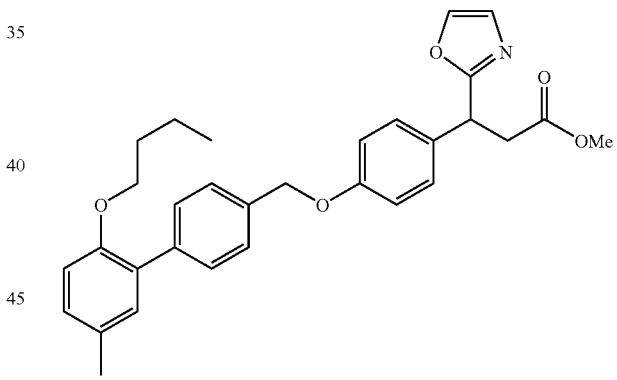

10.6

Methyl 3-[4-(5'-methyl-2'-butoxybiphenylmethoxy)phenyl]-3-(oxazol-2-yl)propanoate (10.6). A mixture of 10.5 (1.02 mmol), 4-(2'-butoxy-5'-methylphenyl)benzyl bromide (1.33 mmol) and cesium carbonate (2.55 mmol) in DMF was stirred at room temperature for 2 hours. The reaction was quenched with water and extracted with EtOAc. The organic phase was washed with brine, dried over anhydrous sodium sulfate, filtered, and concentrated under reduced pressure. The residue was chromatographed (silica gel, 1:3 EtOAc/hexane) and compound 10.6 was obtained. MS ESI (pos.) m/e 500.2 (M+1). $^1$H NMR (500 MHz) (DMSO-d$_6$) δ 8.00 (s, 1H); 7.53(d, J=8Hz, 2H); 7.47 (d, J=8Hz, 2H); 7.21 (d, J=8Hz, 2H); 7.14 (m, 3H); 7.00 (m, 3H); 5.13 (s, 2H); 4.56

(m, 1H); 3.97 (m, 2H); 3.58 (s, 3H); 3.26 (m, 1H); 2.98 (m, 1H); 2.30 (s, 3H); 1.63 (m, 2H); 1.37 (m, 2H); 0.89 (m, 3H).

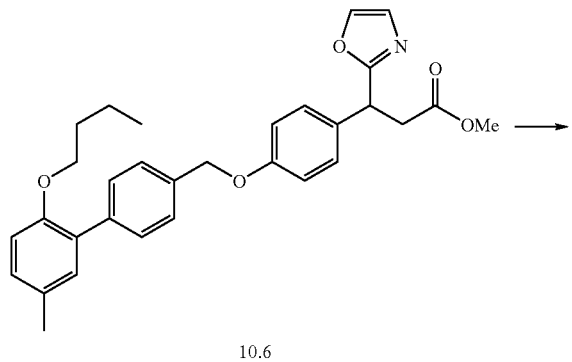

10.6

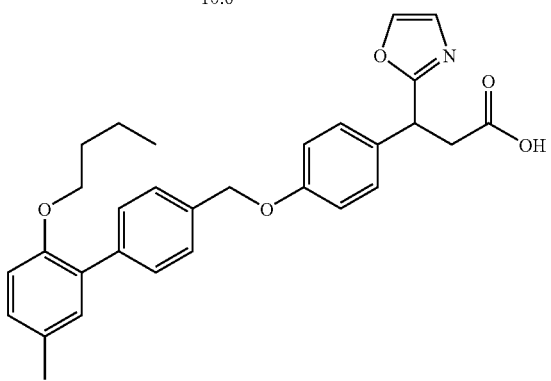

10.7

3-[4-(5'-Methyl-2'-butoxybiphenylmethoxy)phenyl]-3-(oxazol-2-yl)propanoic acid (10.7). A mixture of 10.6 (1.2 mmol), 10% NaOH (aq, 10 mL) and EtOH (22 mL) was stirred at room temperature for 1 hour. After removing EtOH under reduced pressure, the residue was acidified with dilute HCl (1N) to pH 3-4 and extracted with EtOAc. The combined organic extracts were washed with brine, dried over anhydrous sodium sulfate, filtered, and concentrated under reduced pressure. The residue was chromatographed (silica gel, 1:9 MeOH/DCM) and compound 10.7 was obtained. MS ESI (neg.) m/e 484.1(M−1). $^1$H NMR (500 MHz) (DMSO-$d_6$) δ 7.99(m, 1H); 7.53(d, J=8.5 Hz, 2H); 7.46 (d, J=8.5 Hz, 2H); 7.20 (d, J=8.5 Hz, 2H); 7.14(m, 3H), 7.00 (m, 3 H); 5.13 (s, 2H); 4.53 (m, 1H); 3.96 (m, 2H); 3.16-3.31 (m, 1H); 2.83-2.86 (m, 1H); 2.30 (s, 3H); 1.65 (m, 2H); 1.37 (m, 2H); 0.89 (m, 3H).

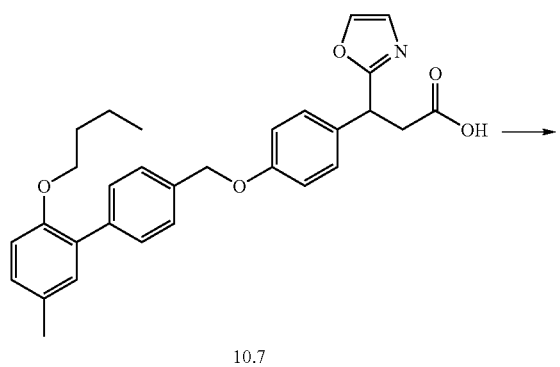

10.7

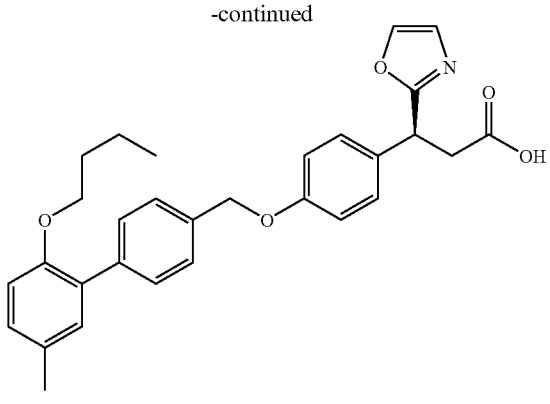

10

(S)-3-[4-(5'-Methyl-2'-butoxybiphenylmethoxy)phenyl]-3-(oxazol-2-yl)propanoic acid (10). The enantiomers of compound 10.7 were separated using Chiral Technologies Inc. CHIRALPAK AD-H column with 10% i-PrOH:hexanes as eluant. The enantiomer with greater retention time 10 (80 mg) was obtained in 92% ee. The absolute configuration of 10 was assigned by analogy to other active GPR40 agonists. MS ESI (neg.) m/e 484.1 (M−H). $^1$H NMR (500 MHz) (DMSO-$d_6$) δ 7.99(m, 1H); 7.53(d, J=8.5 Hz, 2H); 7.46 (d, J=8.5 Hz, 2H); 7.20 (d, J=8.5 Hz, 2H); 7.14(m, 3H), 7.00 (m, 3H); 5.13 (s, 2H); 4.53 (m, 1H); 3.96 (m, 2H); 3.16-3.31 (m, 1H); 2.83-2.86 (m, 1H); 2.30 (s, 3H); 1.65 (m, 2H); 1.37 (m, 2H); 0.89 (m, 3H).

6.11 Example 11

Cell Based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25% (w/v)). Trypsinization was halted with 28 mL of Hanks Buffered Salt Solution containing 20 mM Hepes (H/HBSS) and 0.01% fatty acid-free human serum albumin (HSA). Coelantrazine was added to 1 ug/mL, and the cells were incubated for 2 hours at room temperature. Compounds were dissolved in DMSO for preparation of 10 mM stock solutions. Compounds were diluted in H/HBSS containing either 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The $EC_{50}$ (effective concentration to reach 50% maximal response) was determined from the dose response plot.

Table 1 presents representative data ($EC_{50}$ values) obtained for exemplary compounds of the invention for the relative activation of human GPR40.

The stereoisomers in Table 1 are as specified, i.e., S-enantiomers or R-enantiomers, and if not specified, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

TABLE 1

Aequorin Assay Using Human GPR40

| No. | Structure | Relative EC$_{50}$ |
|-----|-----------|--------------------|
| 4 | 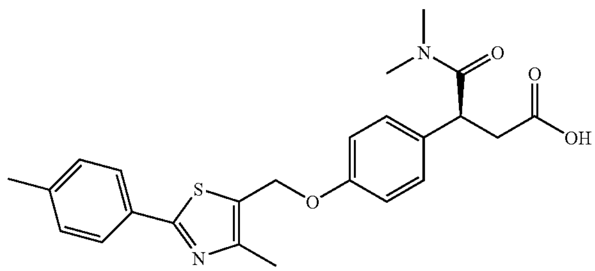 | ++++ |
|   | | ++++ |
| 3 | 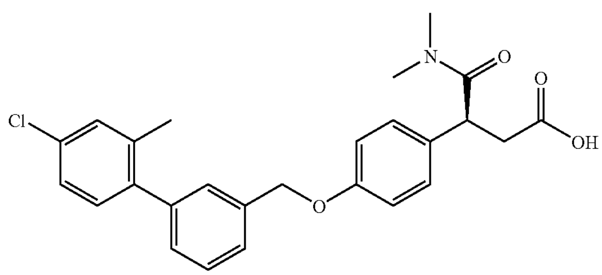 | ++++ |
|   | | ++++ |
|   | | +++ |

TABLE 1-continued
Aequorin Assay Using Human GPR40
| No. | Structure | Relative EC$_{50}$ |
|---|---|---|
| | 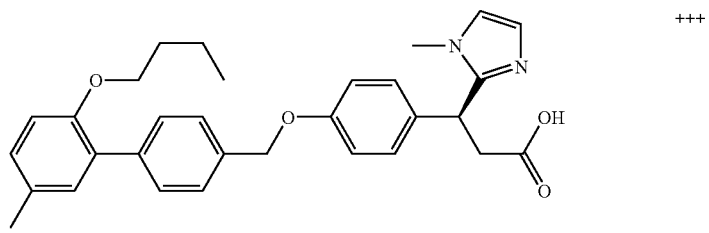 | +++ |
| 9 | 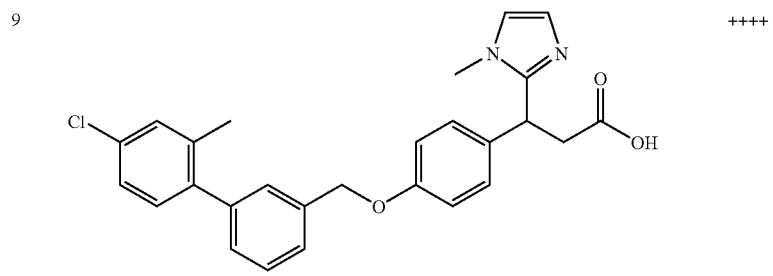 | ++++ |
| | 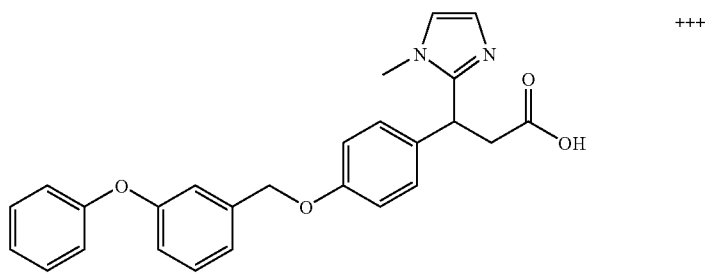 | +++ |
| | 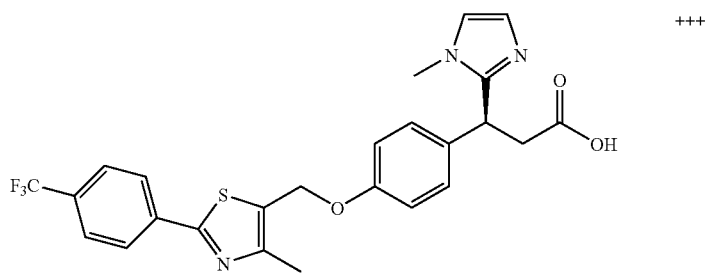 | +++ |
| | 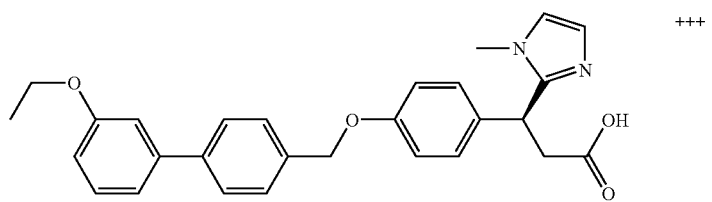 | +++ |

TABLE 1-continued

Aequorin Assay Using Human GPR40

| No. | Structure | Relative EC$_{50}$ |
|---|---|---|
| | (structure) | ++++ |
| | (structure) | ++++ |
| | (structure) | ++++ |
| | (structure) | ++++ |
| | (structure) | +++ |

TABLE 1-continued

Aequorin Assay Using Human GPR40

| No. | Structure | Relative EC$_{50}$ |
|---|---|---|
| 10 | 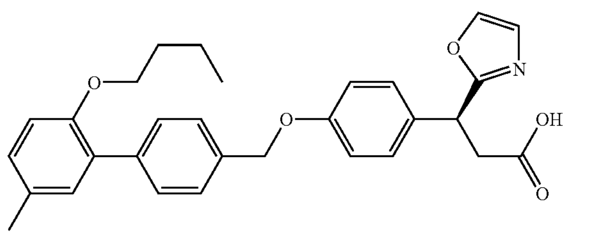 | ++++ |
| | | ++++ |
| | | ++ |
| | | +++ |
| | | +++ |

TABLE 1-continued

Aequorin Assay Using Human GPR40

| No. | Structure | Relative EC$_{50}$ |
|-----|-----------|--------------------|
|   |   | ++++ |
|   |   | ++ |
|   |   | ++++ |
| 5 |   | +++ |
|   |   | +++ |

TABLE 1-continued

Aequorin Assay Using Human GPR40

| No. | Structure | Relative EC$_{50}$ |
|---|---|---|
| 6 | 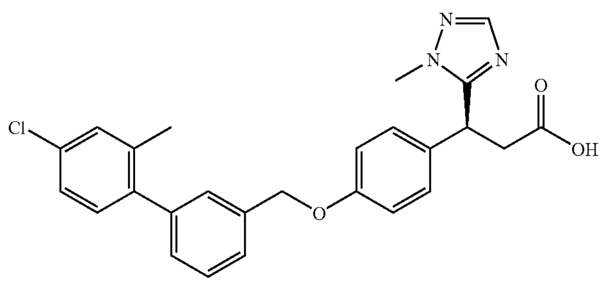 | ++++ |
| | | +++ |
| 7 | 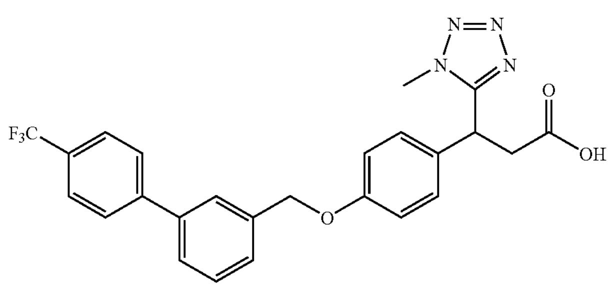 | ++++ |
| | | ++++ |
| | | ++++ |

TABLE 1-continued

Aequorin Assay Using Human GPR40

| No. | Structure | Relative EC$_{50}$ |
|---|---|---|
| 8 | [structure: 4-chloro-2-methylbiphenyl linked via CH$_2$-O to phenyl bearing CH(1-methyltetrazol-5-yl)CH$_2$COOH] | ++++ |
| | [structure: 3-chloro-2-methylbiphenyl linked via CH$_2$-O to phenyl bearing CH(1-methyltetrazol-5-yl)CH$_2$COOH] | +++++ |
| | [structure: 5-chloro-2-methylbiphenyl linked via CH$_2$-O to phenyl bearing CH(1-methyltetrazol-5-yl)CH$_2$COOH] | ++++ |

$^a$EC$_{50}$ Ranges:
+ EC$_{50}$ > 10 μM
++ 1 μM ≤ EC$_{50}$ ≤ 10 μM
+++ 0.1 μM ≤ EC$_{50}$ < 1 μM
++++ 0.01 μM ≤ EC$_{50}$ < 0.1 μM
+++++ EC$_{50}$ < 0.01 μM

6.12 Example 12

Insulin Secretion Assay

Human islets were isolated from cadaveric donors. Islets were treated with trypsin (0.25% (w/v) and cells were seeded in 96-well plates containing 3,000 cells per well. Cells were cultured in Roswell Park Memorial Institute (RMPI) media containing 10% fetal bovine serum.

For determination of insulin secretion, media was removed from islet cells and replaced with Krebs-Ringer bicarbonate buffer containing 10 mM HEPES (KRBH) and 2 mM glucose. After one hour incubation, media was replaced with KRBH conaining 11.2 mM glucose and test compounds. Insulin released into the medium from the islet cells was measured using scintillation proximity assay (SPA). The compounds of Examples 4 and 9 stimulated insulin secretion from islet cells with EC$_{50}$ values of less than 1 uM.

For determination of insulin secretion from rodent islets, C57/B16 mice are euthanized with carbon dioxide gas. The pancreatic bile duct is clamped proximal to the duodenum and then cannulated. H/HBSS containing 0.75 mg/ml collagenase XI (Sigma) is then infused into the pancreas through the cannula. The pancreas is excised and then incubated at 37° C. for 13 minutes to complete enzymatic digestion. The collagenase digestion is quenched in H/HBSS containing 1% BSA and washed once in the same buffer. Islets can be purified using density gradient centrifugation using Histopaque (Sigma) and are hand-picked under a stereomicroscope.

Islets are cultured overnight in Roswell Park Memorial Institute (RMPI) media containing 10% fetal bovine serum and 50 uM beta-mercaptoethanol. Following overnight culture, islets are incubated in KRBHcontaining 2.8 mM glucose for one hour.

For determination of insulin secretion, islets are incubated in DMEM containing 12.5 mM glucose and test compounds for one hour. Insulin released into the culture medium from the islets is measured using an insulin ELISA.

All publications and patent applications cited in this specification are herein incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in l light of the teachings of this invention that certain changes and modifications may be made thereto without departing from the spirit or scope of the appended claims.

What is claimed:

1. A compound of formula (I):

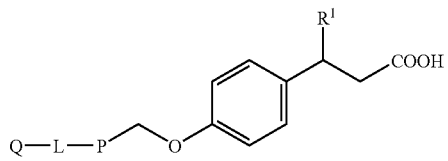

or a pharmaceutically acceptable salt, or ester thereof, wherein
- Q is a phenyl optionally substituted with substituents independently selected from methyl, trifluoromethyl, halogen, methoxy, ethoxy, butoxy, or hydroxyl;
- L is a bond or O;
- P is benzene or a thiazole optionally substituted with a $(C_1$-$C_4)$alkyl group; and
- $R^1$ is an imidazolyl optionally substituted with a $(C_1$-$C_4)$ alkyl group or a triazolyl optionally substituted with a $(C_1$-$C_4)$alkyl group.

2. The compound of claim 1, wherein the compound of formula (I) is a compound of formula (Ia):

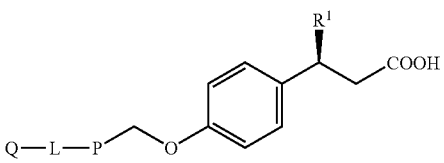

wherein, Q, L, P and $R^1$ are as defined in claim 1.

3. The compound of claim 1, wherein $R^1$ is selected from the group consisting of 1-methyl-1H-imidazol-2-yl and 2-methyl-2H-1,2,4-triazol-3-yl.

4. The compound of claim 1, wherein Q is a phenyl substituted with one or two substituents independently selected from methyl, trifluoromethyl, halogen, methoxy, ethoxy, butoxy and hydroxyl.

5. The compound of claim 1, wherein Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, 4-methyl-phenyl or unsubstituted phenyl.

6. The compound of claim 1, wherein Q is a phenyl substituted with one or two substituents independently selected from methyl, trifluoromethyl, halogen, methoxy, ethoxy, butoxy, or hydroxyl, and L is a bond.

7. The compound of claim 1, wherein Q is an unsubstituted phenyl and L is an O.

8. The compound of claim 1, wherein the compound of formula (I) is a compound of formula (II) or (III):

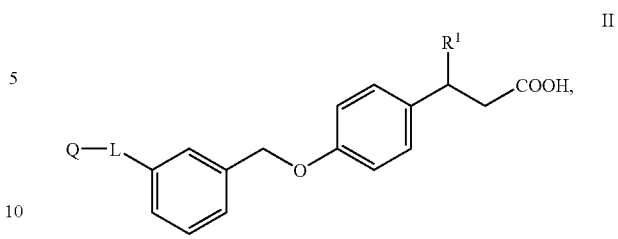

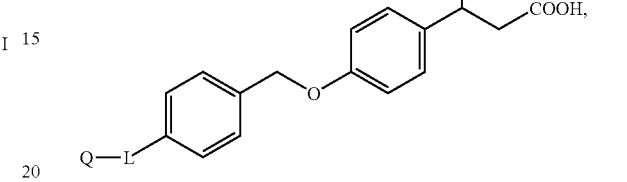

wherein, Q, L and $R^1$ are as defined in claim 1.

9. The compound of claim 8, wherein the compound of formula (I) is a compound of formula (IIa) or (IIIa):

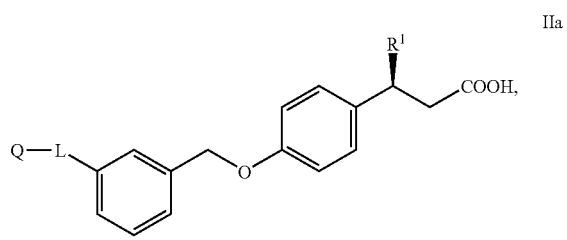

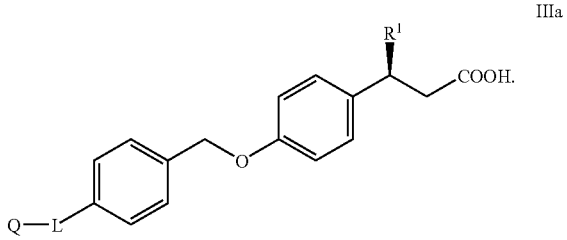

10. The compound of claim 8, wherein $R^1$ is selected from the group consisting of 1-methyl-1H-imidazol-2-yl and 2-methyl-2H-1,2,4-triazol-3-yl.

11. The compound of claim 10, wherein Q is an unsubstituted phenyl and L is an O.

12. The compound of claim 11, wherein the compound is selected from
- (S)-3-(1-Methyl-1H-imidazol-2-yl)-3-[4-(3-phenoxybenzyloxy)-phenyl]-propionic acid;
- (S)-3-(2-Methyl-2H-1,2,4-triazol-3-yl)-3-[4-(3-phenoxybenzyloxy)-phenyl]-propionic acid;
- (S)-3-(1-Methyl-1H-imidazol-2-yl)-3-[4-(4-phenoxybenzyloxy)-phenyl]-propionic acid; or
- (S)-3-(2-Methyl-2H-1,2,4-triazol-3-yl)-3-[4-(4-phenoxybenzyloxy)-phenyl]-propionic acid; or a pharmaceutically acceptable salt thereof.

13. The compound of claim 10, wherein Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, or 4-methyl-phenyl.

14. The compound of claim 13, wherein L is a bond.

15. The compound of claim 14, wherein the compound is selected from
- (S)-3-(1-Methyl-1H-imidazol-2-yl)-3-[4-(4'-trifluoromethyl-biphenyl-3-ylmethoxy)-phenyl]-propionic acid;
- (S)-3-(2-Methyl-2H-1,2,4-triazol-3-yl)-3-[4-(4'-trifluoromethyl-biphenyl-3-ylmethoxy)- phenyl]-propionic acid;
- (S)-3-[4-(3'-Chloro-2'-methyl-biphenyl-3-ylmethoxy)-phenyl]-3-(1-methyl-1H-imidazol-2- yl)-propionic acid;
- (S)-3-[4-(3'-Chloro-2'-methyl-biphenyl-3-ylmethoxy)-phenyl]-3-(2-methyl-2H-1,2,4-triazol-3- yl)-propionic acid,
- (S)-3-[4-(4'-Chloro-2'-methyl-biphenyl-3-ylmethoxy)-phenyl]-3-(1-methyl-1H-imidazol-2- yl)-propionic acid;
- (S)-3-[4-(4'-Chloro-2'-methyl-biphenyl-3-ylmethoxy)-phenyl]-3-(2-methyl-2H-1,2,4-triazol-3- yl)-propionic acid;
- (S)-3-[4-(5'-Chloro-2'-methyl-biphenyl-3-ylmethoxy)-phenyl]-3-(1-methyl-1H-imidazol-2- yl)-propionic acid;
- (S)-3-[4-(5'-Chloro-2'-methyl-biphenyl-3-ylmethoxy)-phenyl]-3-(2-methyl-2H-1,2,4-triazol-3- yl)-propionic acid;
- (S)-3-[4-(2'-Butoxy-5'-methyl-biphenyl-4-ylmethoxy)-phenyl]-3-(1-methyl-1H-imidazol-2- yl)-propionic acid;
- (S)-3-[4-(2'-Butoxy-5'-methyl-biphenyl-4-ylmethoxy)-phenyl]-3-(2-methyl-2H-1,2,4-triazol- 3-yl)-propionic acid;
- (S)-3-[4-(3'-Ethoxy-biphenyl-4-ylmethoxy)-phenyl]-3-(1-methyl-1H-imidazol-2-yl)-propionic acid; or
- (S)-3-[4-(3'-Ethoxy-biphenyl-4-ylmethoxy)-phenyl]-3-(2-methyl-2H-1,2,4-triazol-3-yl)- propionic acid; or
- a pharmaceutically acceptable salt thereof.

16. The compound of claim 1, wherein the compound of formula (I) is a compound of formula (V):

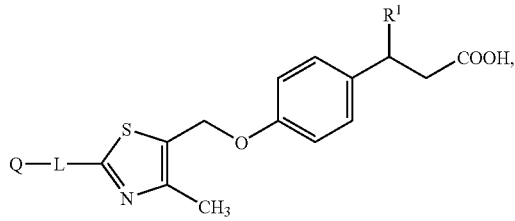

V wherein, Q, L and $R^1$ are as defined in claim 1.

17. The compound of claim 16, wherein the compound of formula (I) is a compound of formula (Va):

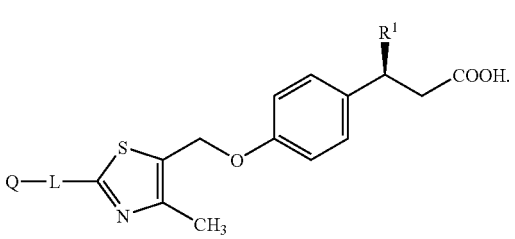

Va

18. The compound of claim 16, wherein $R^1$ is selected from the group consisting of 1-methyl-1H-imidazol-2-yl and 2-methyl-2H-1,2,4-triazol-3-yl.

19. The compound of claim 18, wherein L is a bond.

20. The compound of claim 19, wherein Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, or 4-methyl-phenyl.

21. The compound of claim 20, wherein the compound is selected from
- (S)-3-(1-Methyl-1H-imidazol-2-yl)-3-{4-[4-methyl-2-(4-trifluoromethyl-phenyl)-thiazol-5- ylmethoxy]-phenyl}-propionic acid;
- (S)-3-(2-Methyl-2H-1,2,4-triazol-3-yl)-3-{4-[4-methyl-2-(4-trifluoromethyl-phenyl)-thiazol- 5-ylmethoxy]-phenyl}-propionic acid;
- (S)-3-(1-Methyl-1H-imidazol-2-yl)-3-[4-(4-methyl-2-p-tolyl-thiazol-5-ylmethoxy)-phenyl]- propionic acid; or
- (S)-3-[4-(4-Methyl-2-p-tolyl-thiazol-5-ylmethoxy)-phenyl]-3-(2-methyl-2H-1,2,4-triazol-3- yl)-propionic acid; or
- a pharmaceutically acceptable salt thereof.

22. A pharmaceutical composition, comprising a pharmaceutically acceptable carrier, diluent or excipient and the compound of claim 1.

23. The pharmaceutical composition of claim 22, wherein the compound is selected from
- (S)-3-[4-(4'-Chloro-2'-methyl-biphenyl-3-ylmethoxy)-phenyl]-3-(1-methyl-1H-imidazol-2- yl)-propionic acid;
- (S)-3-[4-(4'-Chloro-2'-methyl-biphenyl-3-ylmethoxy)-phenyl]-3-(2-methyl-2H-1,2,4-triazol-3- yl)-propionic acid; or
- (S)-3-[4-(2'-Butoxy-5'-methyl-biphenyl-4-ylmethoxy)-phenyl]-3-(2-methyl-2H-1,2,4-triazol- 3-yl)-propionic acid; or
- a pharmaceutically acceptable salt thereof.

24. A method for activating GPR40 function in a cell, comprising contacting the cell with the compound of claim 1.

25. A compound of formula (I):

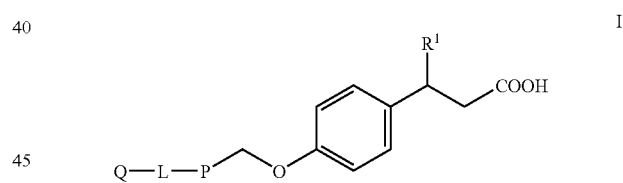

I or a pharmaceutically acceptable salt, or ester thereof, wherein
- Q is a phenyl optionally substituted with substituents independently selected from methyl, trifluoromethyl, halogen, methoxy, ethoxy, butoxy, or hydroxyl;
- L is a bond or O;
- P is benzene or a thiazole optionally substituted with a $(C_1-C_4)$alkyl group;
- $R^1$ is an oxazolyl optionally substituted with a $(C_1-C_4)$alkyl group, wherein the optionally substituted oxazolyl is other than 5-methyl-oxazol-2-yl; a tetrazolyl optionally substituted with a $(C_1-C_4)$alkyl group; or —C(O)NR$^2$R$^3$; and
- $R^2$ and $R^3$ are independently selected from hydrogen and $(C_1-C_4)$alkyl;

with the proviso that when Q is 4-trifluoromethyl-phenyl, P is benzene and L is a bond, then $R^1$ is not dimethylcarbamyl or —C(═O)NH$_2$, with the further proviso that when Q is 4-trifluoromethyl-phenyl, P is benzene and L is a bond, then $R^1$ is not an unsubstituted tetrazolyl.

26. The compound of claim 25, wherein the compound of formula (I) is a compound of formula (Ia):

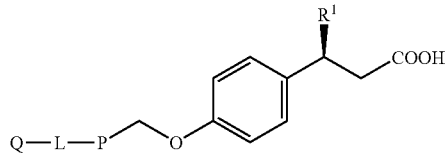

wherein, Q, L, P and $R^1$ are as defined in claim 25.

27. The compound of claim 25, wherein $R^1$ is selected from the group consisting of dimethylcarbamyl, oxazol-2-yl, and 1-methyl-1H-tetrazol-5-yl.

28. The compound of claim 25, wherein Q is a phenyl substituted with one or two substituents independently selected from methyl, trifluoromethyl, halogen, methoxy, ethoxy, butoxy and hydroxyl.

29. The compound of claim 25, wherein Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, 4-methyl-phenyl or unsubstituted phenyl.

30. The compound of claim 25, wherein Q is an unsubstituted phenyl and L is an O.

31. The compound of claim 25, wherein Q is a phenyl substituted with one or two substituents independently selected from methyl, trifluoromethyl, halogen, methoxy, ethoxy, butoxy and hydroxyl, and L is a bond.

32. The compound of claim 25, wherein the compound of formula (I) is a compound of formula (II) or (III):

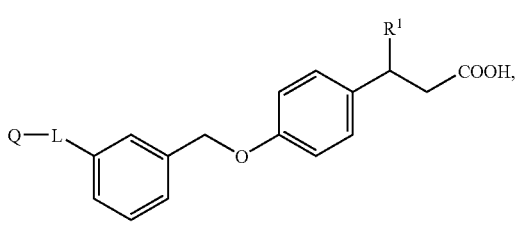

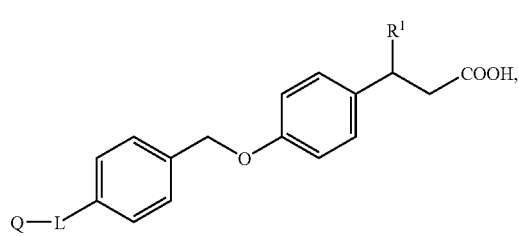

wherein, Q, L and $R^1$ are as defined in claim 25.

33. The compound of claim 32, wherein the compound of formula (I) is a compound of formula (IIa) or (IIIa):

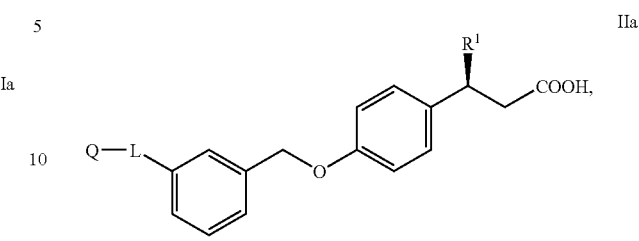

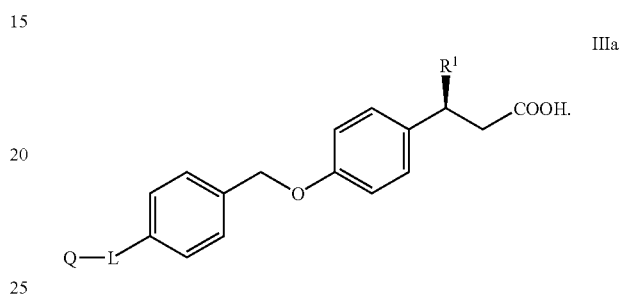

34. The compound of claim 32, wherein $R^1$ is selected from the group consisting of dimethylcarbamyl, oxazol-2-yl, and 1-methyl-1H-tetrazol-5-yl.

35. The compound of claim 34, wherein Q is an unsubstituted phenyl and L is an O.

36. The compound of claim 35, wherein the compound is selected from
(S)-N,N-Dimethyl-3-[4-(3-phenoxy-benzyloxy)-phenyl]-succinamic acid;
(S)-3-Oxazol-2-yl-3-[4-(3-phenoxy-benzyloxy)-phenyl]-propionic acid;
(S)-3-(1-Methyl-1H-tetrazol-5-yl)-3-[4-(3-phenoxy-benzyloxy)-phenyl]-propionic acid;
(S)-N,N-Dimethyl-3-[4-(4-phenoxy-benzyloxy)-phenyl]-succinamic acid;
(S)-3-Oxazol-2-yl-3-[4-(4-phenoxy-benzyloxy)-phenyl]-propionic acid; or
(S)-3-(1-Methyl-1H-tetrazol-5-yl)-3-[4-(4-phenoxy-benzyloxy)-phenyl]-propionic acid; or
a pharmaceutically acceptable salt thereof.

37. The compound of claim 34, wherein Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, or 4-methyl-phenyl.

38. The compound of claim 34, wherein L is a bond.

39. The compound of claim 38, wherein the compound is selected from
(S)-3-Oxazol-2-yl-3-[4-(4'-trifluoromethyl-biphenyl-3-ylmethoxy)-phenyl]-propionic acid;
(S)-3-(1-Methyl-1H-tetrazol-5-yl)-3-[4-(4'-trifluoromethyl-biphenyl-3-ylmethoxy)-phenyl]- propionic acid;
(S)-3-[4-(3'-Chloro-2'-methyl-biphenyl-3-ylmethoxy)-phenyl]-N,N-dimethyl-succinamic acid;
(S)-3-[4-(3'-Chloro-2'-methyl-biphenyl-3-ylmethoxy)-phenyl]-3-oxazol-2-yl-propionic acid;
(S)-3-[4-(3'-Chloro-2'-methyl-biphenyl-3-ylmethoxy)-phenyl]-3-(1-methyl-1H-tetrazol-5-yl)- propionic acid;

(S)-3-[4-(4'-Chloro-2'-methyl-biphenyl-3-ylmethoxy)-phenyl]-N,N-dimethyl-succinamic acid;
(S)-3-[4-(4'-Chloro-2'-methyl-biphenyl-3-ylmethoxy)-phenyl]-3-oxazol-2-yl-propionic acid;
(S)-3-[4-(4'-Chloro-2'-methyl-biphenyl-3-ylmethoxy)-phenyl]-3-(1-methyl-1H-tetrazol-5-yl)- propionic acid;
(S)-3-[4-(5'-Chloro-2'-methyl-biphenyl-3-ylmethoxy)-phenyl]-N,N-dimethyl-succinamic acid;
(S)-3-[4-(5'-Chloro-2'-methyl-biphenyl-3-ylmethoxy)-phenyl]-3-oxazol-2-yl-propionic acid;
(S)-3-[4-(5'-Chloro-2'-methyl-biphenyl-3-ylmethoxy)-phenyl]-3-(1-methyl-1H-tetrazol-5-yl)- propionic acid;
(S)-3-[4-(2'-Butoxy-5'-methyl-biphenyl-4-ylmethoxy)-phenyl]-N,N-dimethyl-succinamic acid;
(S)-3-[4-(2'-Butoxy-5'-methyl-biphenyl-4-ylmethoxy)-phenyl]-3-oxazol-2-yl-propionic acid;
(S)-3-[4-(2'-Butoxy-5'-methyl-biphenyl-4-ylmethoxy)-phenyl]-3-(1-methyl-1H-tetrazol-5-yl)- propionic acid;
(S)-3-[4-(3'-Ethoxy-biphenyl-4-ylmethoxy)-phenyl]-N,N-dimethyl-succinamic acid;
(S)-3-[4-(3'-Ethoxy-biphenyl-4-ylmethoxy)-phenyl]-3-oxazol-2-yl-propionic acid; or
(S)-3-[4-(3'-Ethoxy-biphenyl-4-ylmethoxy)-phenyl]-3-(1-methyl-1H-tetrazol-5-yl)-propionic acid; or
a pharmaceutically acceptable salt thereof.

40. The compound of claim 25, wherein the compound of formula (I) is a compound of formula (V):

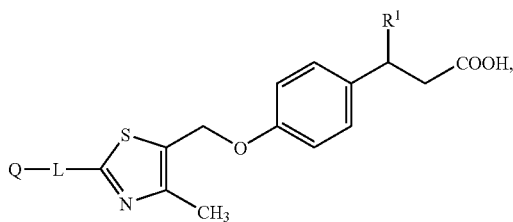

wherein, Q, L and $R^1$ are as defined in claim 25.

41. The compound of claim 40, wherein the compound of formula (I) is a compound of formula (Va):

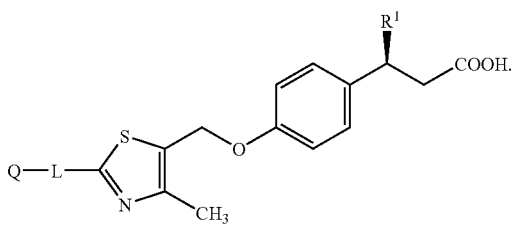

42. The compound of claim 40, wherein $R^1$ is selected from the group consisting of dimethylcarbamyl, oxazol-2-yl, and 1-methyl-1H-tetrazol-5-yl.

43. The compound of claim 42, wherein L is a bond.

44. The compound of claim 43, wherein Q is 4-trifluoromethyl-phenyl, 3-chloro-2-methyl-phenyl, 4-chloro-2-methyl-phenyl, 5-chloro-2-methyl-phenyl, 5-methyl-2-butoxy-phenyl, 3-ethoxy-phenyl, or 4-methyl-phenyl.

45. The compound of claim 44, wherein the compound is selected from
(S)-N,N-Dimethyl-3-{4-[4-methyl-2-(4-trifluoromethyl-phenyl)-thiazol-5-ylmethoxy]- phenyl}-succinamic acid;
(S)-3-{4-[4-Methyl-2-(4-trifluoromethyl-phenyl)-thiazol-5-ylmethoxy]-phenyl}-3-oxazol-2- yl-propionic acid;
(S)-3-(1-Methyl-1H-tetrazol-5-yl)-3-{4-[4-methyl-2-(4-trifluoromethyl-phenyl)-thiazol-5- ylmethoxy]-phenyl}-propionic acid;
(S)-N,N-Dimethyl-3-[4-(4-methyl-2-p-tolyl-thiazol-5-ylmethoxy)-phenyl]- succinamic acid;
(S)-3-[4-(4-Methyl-2-p-tolyl-thiazol-5-ylmethoxy)-phenyl]-3-oxazol-2-yl-propionic acid; or
(S)-3-(1-Methyl-1H-tetrazol-5-yl)-3-[4-(4-methyl-2-p-tolyl-thiazol-5-ylmethoxy)-phenyl]- propionic acid; or
a pharmaceutically acceptable salt thereof.

46. A pharmaceutical composition, comprising a pharmaceutically acceptable carrier, diluent or excipient and the compound of claim 25.

47. The pharmaceutical composition of claim 46, wherein the compound is selected from
(S)-3-[4-(4'-Chloro-2'-methyl-biphenyi-3-ylmethoxy)-phenyl]-N,N-dimethyl-succinamic acid;
(S)-3-[4-(4'-Chloro-2'-methyl-biphenyl-3-ylmethoxy)-phenyl]-3-(1-methyl-1H-tetrazol-5-yl)- propionic acid;
(S)-N,N-Dimethyl-3-[4-(4-methyl-2-p-tolyl-thiazol-5-ylmethoxy)-phenyl]- succinamic acid; or
(S)-3-(1-Methyl-1H-tetrazol-5-yl)-3-[4-(4-methyl-2-p-tolyl-thiazol-5-ylmethoxy)-phenyl]- propionic acid; or
a pharmaceutically acceptable salt thereof.

48. A method for activating GPR40 function in a cell, comprising contacting the cell with the compound of claim 25.

* * * * *